US011456064B2

(12) United States Patent
Mobarakeh

(10) Patent No.: US 11,456,064 B2
(45) Date of Patent: Sep. 27, 2022

(54) SYSTEM AND METHOD FOR MEDICAL PLATFORM EMPLOYING ARTIFICIAL INTELLIGENCE AND WEARABLE DEVICES

(71) Applicant: Behjat Iranpour Mobarakeh, Potomac, MD (US)

(72) Inventor: Behjat Iranpour Mobarakeh, Potomac, MD (US)

( * ) Notice: Subject to any disclaimer, the term of this patent is extended or adjusted under 35 U.S.C. 154(b) by 150 days.

(21) Appl. No.: 16/632,512

(22) PCT Filed: Aug. 24, 2018

(86) PCT No.: PCT/US2018/048009
§ 371 (c)(1),
(2) Date: Jan. 20, 2020

(87) PCT Pub. No.: WO2019/040908
PCT Pub. Date: Feb. 28, 2019

(65) Prior Publication Data
US 2021/0166793 A1    Jun. 3, 2021

Related U.S. Application Data

(60) Provisional application No. 62/550,364, filed on Aug. 25, 2017.

(51) Int. Cl.
*G16H 10/60* (2018.01)
*G16H 40/67* (2018.01)
*G16H 50/20* (2018.01)
*A61B 5/00* (2006.01)
*G06Q 30/02* (2012.01)

(52) U.S. Cl.
CPC ........... *G16H 10/60* (2018.01); *A61B 5/0022* (2013.01); *A61B 5/6802* (2013.01); *G06Q 30/0201* (2013.01); *G16H 40/67* (2018.01); *G16H 50/20* (2018.01)

(58) Field of Classification Search
CPC ........ G16H 10/60; G16H 40/67; G16H 50/20; A61B 5/0022; A61B 5/6802; G06Q 30/0201
USPC ....................................................... 705/2–3
See application file for complete search history.

(56) References Cited

U.S. PATENT DOCUMENTS

| | | | |
|---|---|---|---|
| 2009/0177495 A1* | 7/2009 | Abousy | G16H 50/20 705/3 |
| 2014/0081659 A1* | 3/2014 | Nawana | G16H 50/50 705/3 |
| 2015/0216413 A1* | 8/2015 | Soyao | G16H 10/60 709/204 |
| 2017/0323485 A1* | 11/2017 | Samec | A61B 5/6898 |

* cited by examiner

*Primary Examiner* — Michael Tomaszewski

(57) ABSTRACT

A system, method and computer program product for a medical platform, including a wearable device configured to collect implicit and explicit patient information; a database configured to receive the implicit and explicit patient information from the wearable device and generate aggregated patient information; a machine learning system configured to receive the aggregated patient information from the database and generate personalized patient intervention information; and a patient user interface configured to receive patient intervention information.

7 Claims, 24 Drawing Sheets

FIG. 2  Focusing on Cancer, Smoking and Depression Conditions with High Comorbidity.

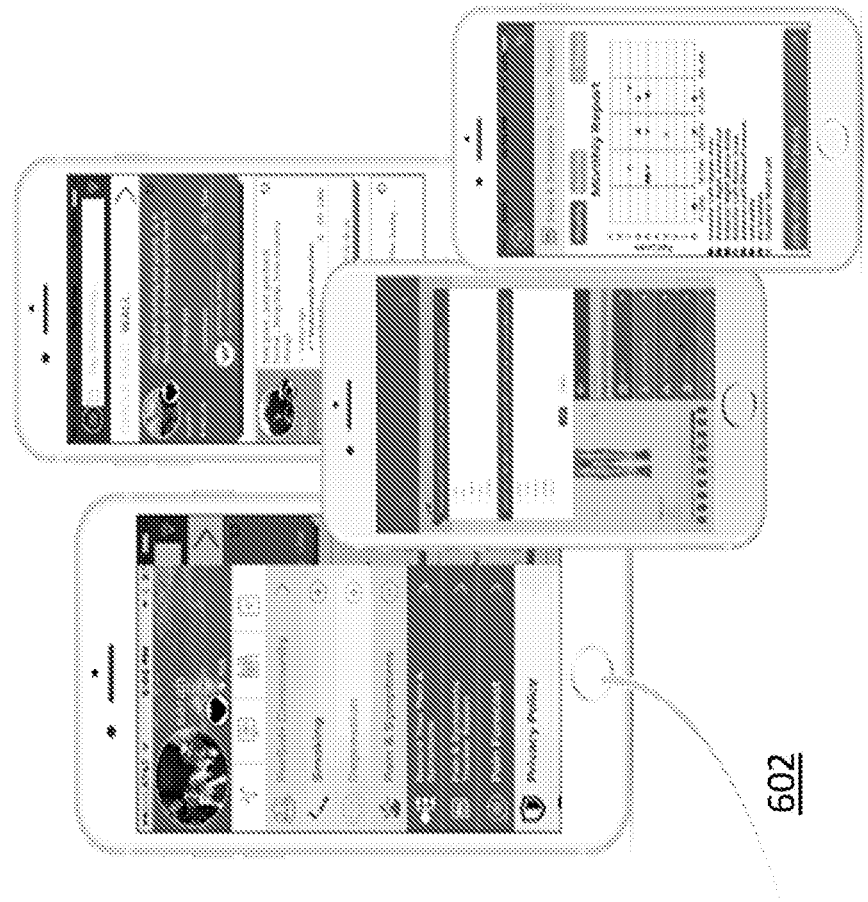
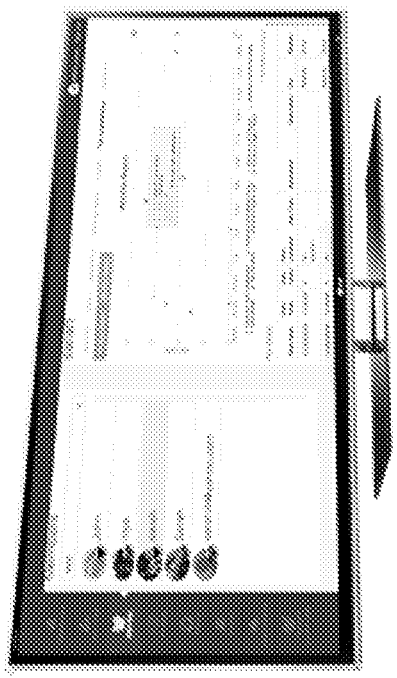
FIG. 6

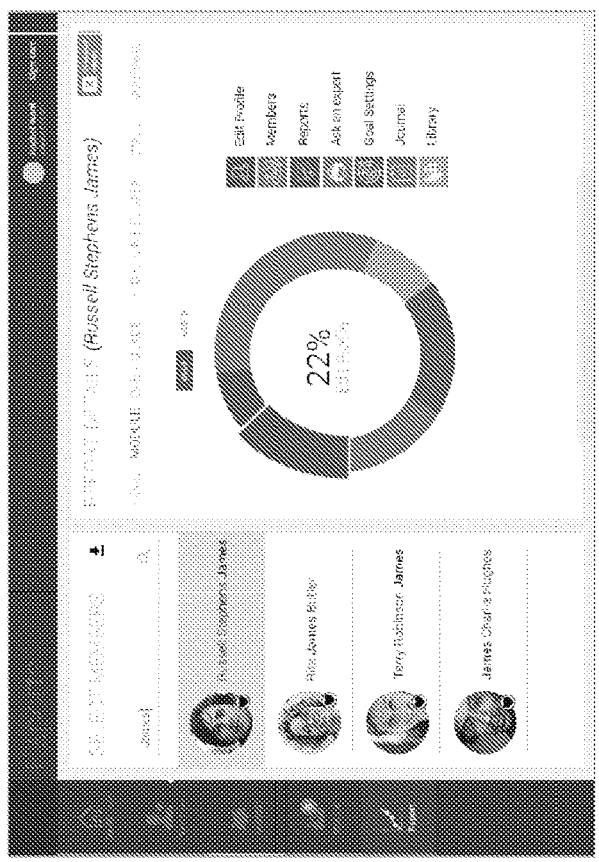
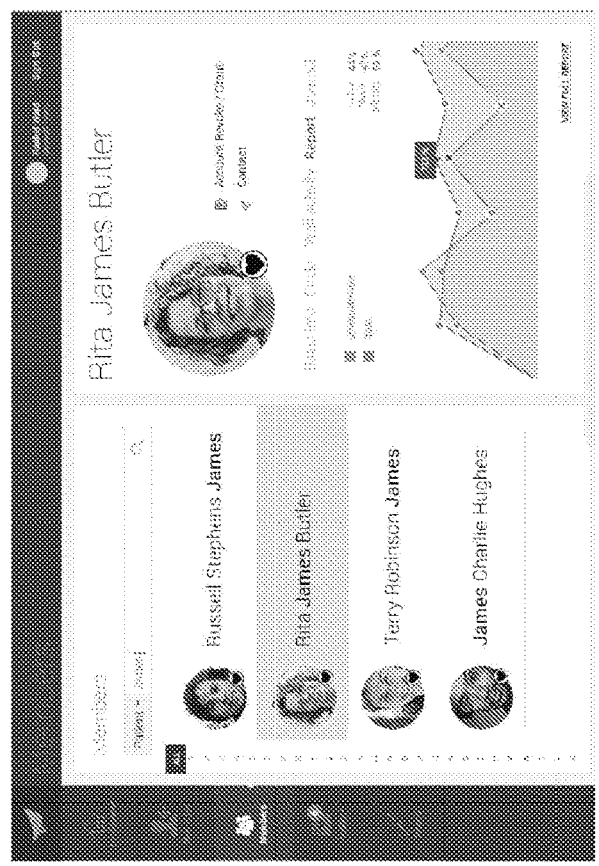
FIG. 7

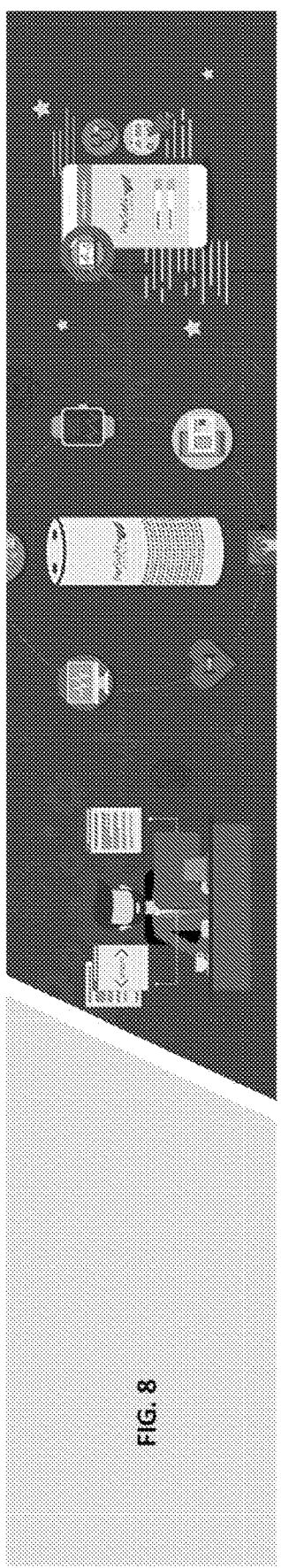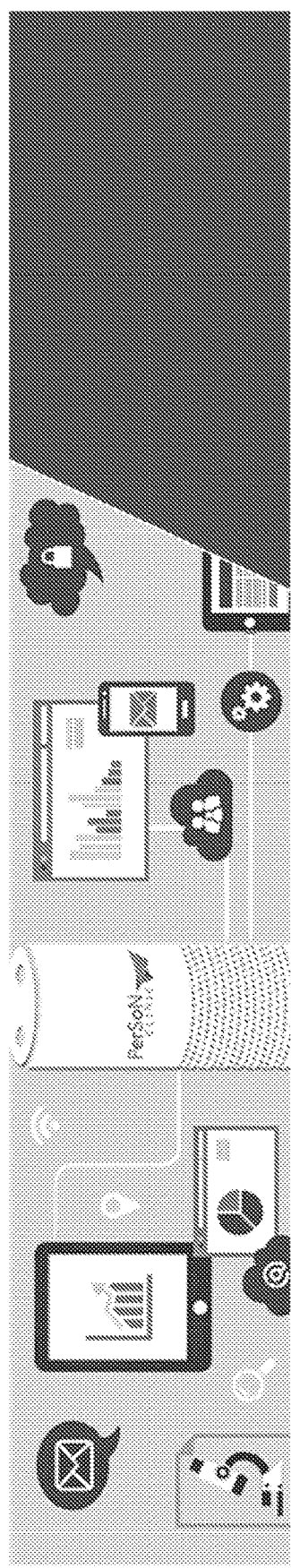
FIG. 8
PerSoN Clinic Health Care

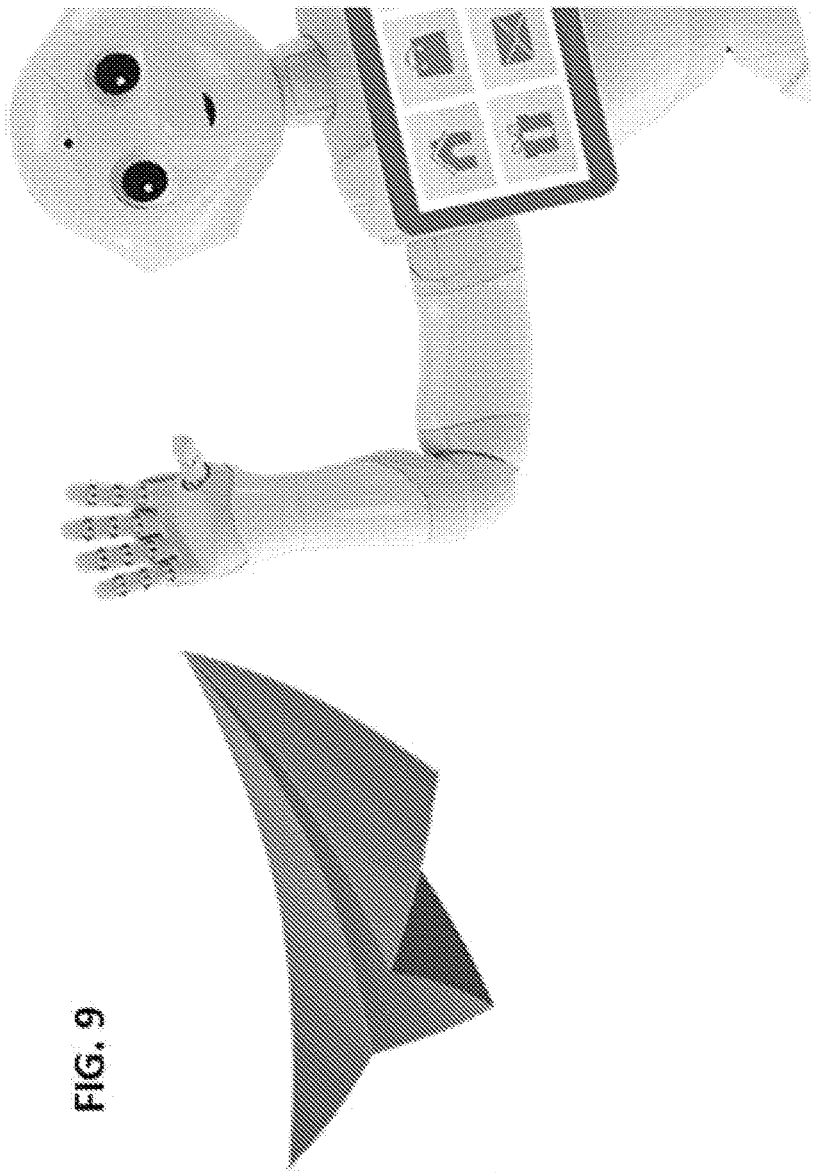
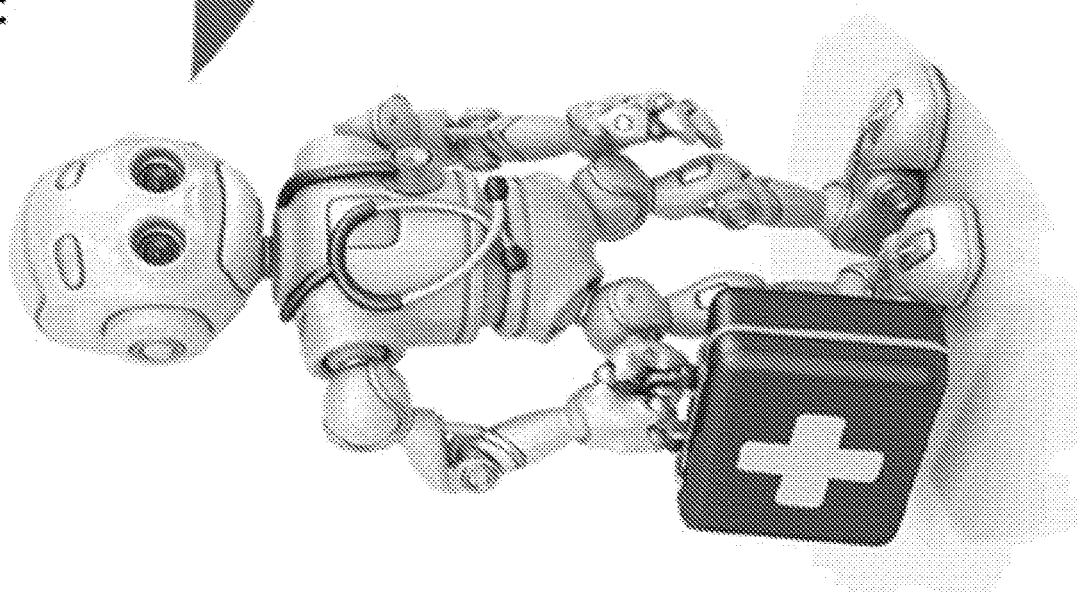
FIG. 9

SYSTEM AND METHOD FOR MEDICAL PLATFORM EMPLOYING ARTIFICIAL INTELLIGENCE AND WEARABLE DEVICES

CROSS REFERENCE TO RELATED DOCUMENTS

The present invention claims priority to U.S. Provisional Patent Application Ser. No. 62/550,364 of Behjat IRANPOUR MOBARAKEH, entitled "MEDICAL PLATFORM," filed on 25 Aug. 2017, the entire disclosure of which is hereby incorporated by reference herein.

BACKGROUND OF THE INVENTION

Field of the Invention

The present invention generally relates to systems and methods for medical platforms, and more particularly to a method, system and computer program product for a medical platform employing artificial intelligence and wearable devices, and the like.

Discussion of the Background

Interconnection of diseases and their effect on human physical, mental and behavioral health is a complex matter that results in a complex treatment with multiple factors in management thereof. There is a huge demand for personalized early intervention and treatment. Despite the advances in genetics and the understanding of the genetic influences on human behavior and hereditary diseases, we know little about non-genetic influences, known collectively as the personal environment, for example, including climate, social and economic settings related to the person, on overall person's physical, mental, and behavioral health, and the like. Furthermore, current systems and methods fail to measure objectively, for example, emotional and physical responses of a person, such as pain, mood, and the like, to external stressors, including economic, social, climate factors, and the like.

There has been revolutionary advancement in machine learning methods, artificial intelligent computing, voice recognition and communication technologies in the last 20 years. Such technological advancements have changed the way humans communicate with each other, particularly, millennial and younger generations. Communicating over voice with intelligent robots and text messaging and using social networking platform to discuss health related issues with doctors, health professionals, care givers and care providers are common. Many care providers use care delivery using such systems. In addition, there is a gap in connecting and mining such data sets and empowering and enabling patients with tools, and the like, so they can participate in designing a most effective and personalized treatment, and the like. However, the invention and embodiments described herein, have not been addressed or presented in any prior art.

SUMMARY OF THE INVENTION

Therefore, there is a need for a method and system that addresses the above and other problems. The above and other problems are addressed by the illustrative embodiments of the present invention, which provide in illustrative embodiments, for example, a method, system and computer program product for a medical platform employing artificial intelligence and wearable devices, and the like, including a social network, a security module, a privacy module, and the like, advantageously, employed for treatment, prevention, and the like, with a feedback module, to improve system performance, and the like.

Accordingly, in illustrative aspects of the present invention there is provided a system for***BASED ON FINAL CLAIMS Still other aspects, features, and advantages of the present invention are readily apparent from the following detailed description, by illustrating a number of illustrative embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIG. 6 is used to illustrate a system and method for a patient centric, collaborative, chronic condition engagement and management platform;

FIG. 7 is used to illustrate a comprehensive patient remote monitoring dashboard for a researcher and a care provider;

FIG. 8 is used to illustrate a Patient Controlled Health ECO-system (PCH ECO-system) infrastructure;

FIG. 9 is used to illustrate a voice enable personal assistant of the PCH ECO-system;

DETAILED DESCRIPTION OF THE PREFERRED EMBODIMENTS

An illustrative system, method and computer program product for a medical platform employing artificial intelligence and wearable devices, and the like, are described. In the following description, for purposes of explanation, numerous specific details are set forth in order to provide a thorough understanding of the present invention. It is apparent to one skilled in the science, however, that the present invention may be practiced without these specific details or with an equivalent arrangement or with one module deployed in the absence of the other. In some instances, well-known devices and structures are shown in block diagram in order to avoid unnecessarily obscuring the present invention. The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

Figure 1:
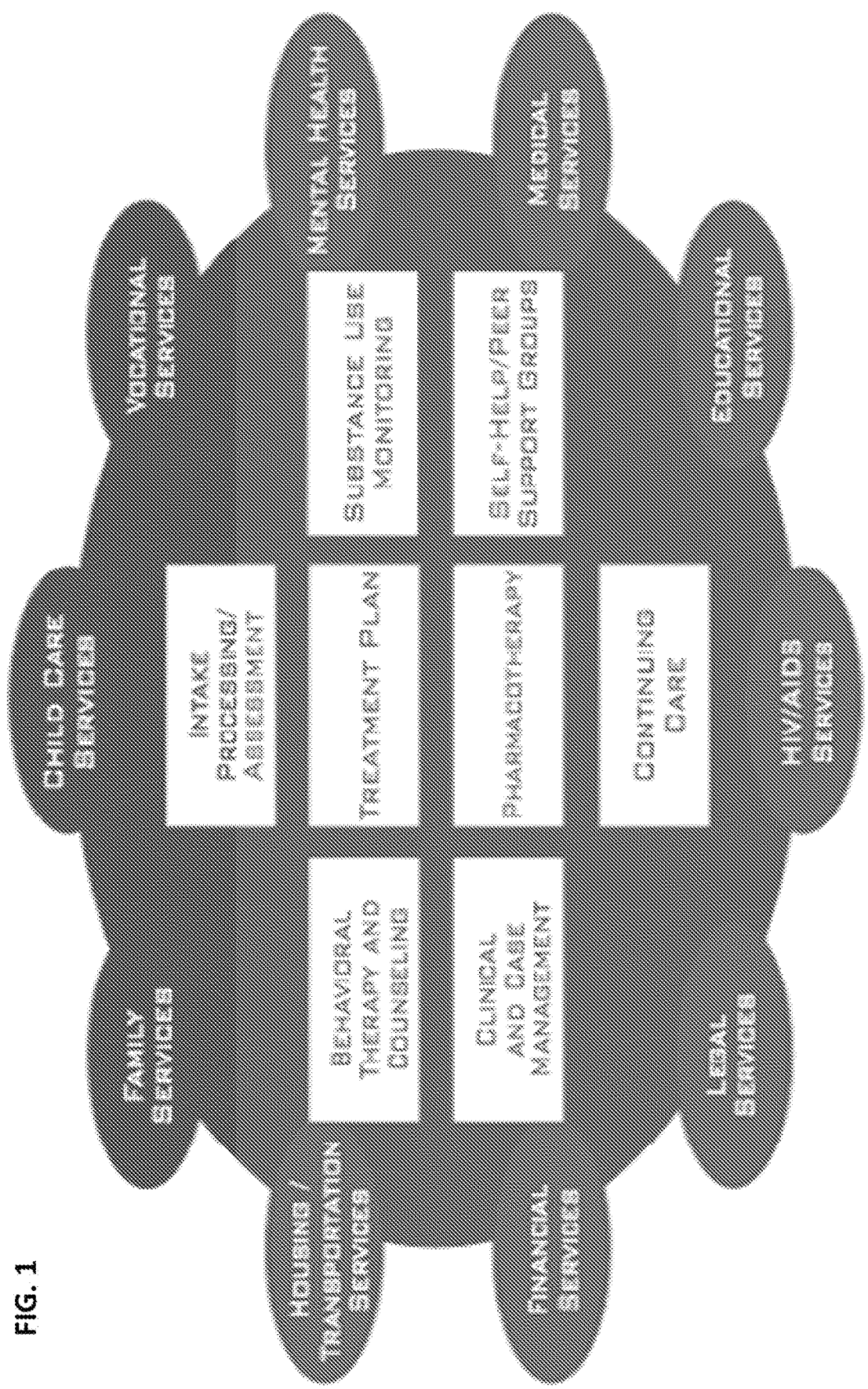
FIG. 1 is used to illustrate components and factors that effect a patient's health and treatment result.

Referring now to the figures, wherein like reference numerals designate identical or corresponding parts throughout the several views, and more particularly in FIGS. 1-24 thereof there is illustrated a method, system, and computer program product, for example, including a platform, for medical field to support effective treatment delivery system and research on mental and/or multi-chronic disease conditions, and the like. Such a medical platform offers services that have been identified by researchers as advantageous for effective mental health and behavioral therapy support system, for example, as shown in FIG. 1 that is used to illustrate components and factors that effect a patient's health and treatment result, and the like.

Accordingly, in an illustrative embodiment, for example, a machine learning engine (MLE) analyzes environmental information, public records, user-provided feedback information (e.g., patient pin, individual bio sensor, brain wave data), collected information from built-in private circle, support social networking system and built-in public forum, care-giver feedback data, individual clinical data, and/or genomic and real time biomarker feedback data, and the like, to create fuzzy data sets that predict a potential human behavior and/or clinical diagnostic, which in turn provides a warning to the user and/or caregiver (e.g., including individual who have legal permission to access these data) of a potential human behavior, delivering personalized clinical and/or behavioral intervention and treatment, and the like. The intervention and/or treatment can be delivered through a mobile based interface and/or wearable device, and the like.

Figure 2:
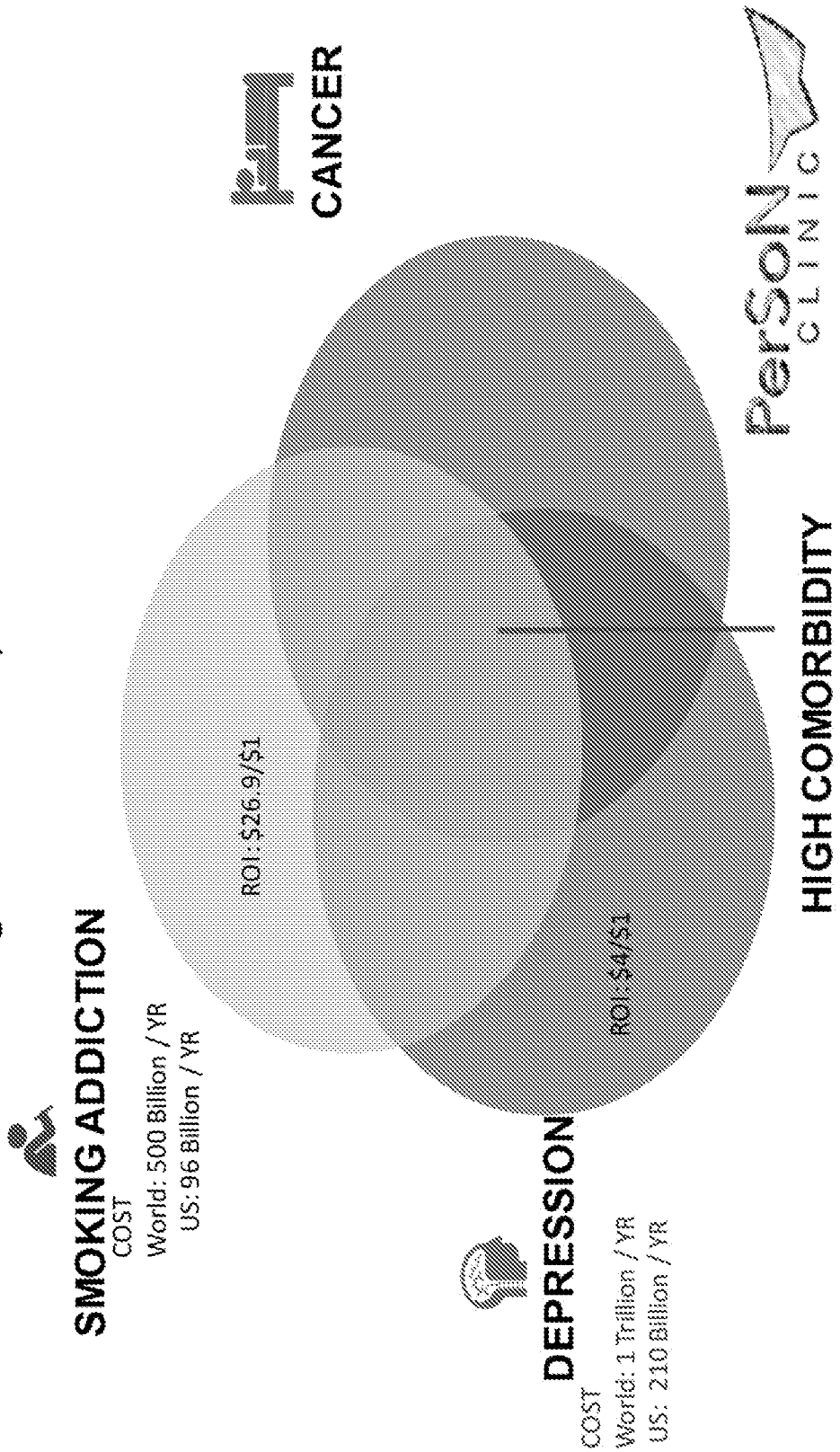
FIG. 2 is used to illustrate high comorbidity among various disease.

FIG. 2 is used to illustrate high comorbidity among various disease, and the like. In FIG. 2, displayed are the high comorbidity among deadly diseases, for example, including Cancer, Depression and Smoking addiction, and the like, with serious considerations (e.g., as further illustrated in FIG. 5), which call for a comprehensive disease management approach to discover the effect of interconnection of such diseases on human physical, mental and behavioral health, and the like, as well as the effect thereof on the results of a complex treatment with multiple factors in managing of them individually or together. Social support and continuum of care is an advantageous component that results in better treatment outcome for any suitable behavioral therapy.

Figure 3:
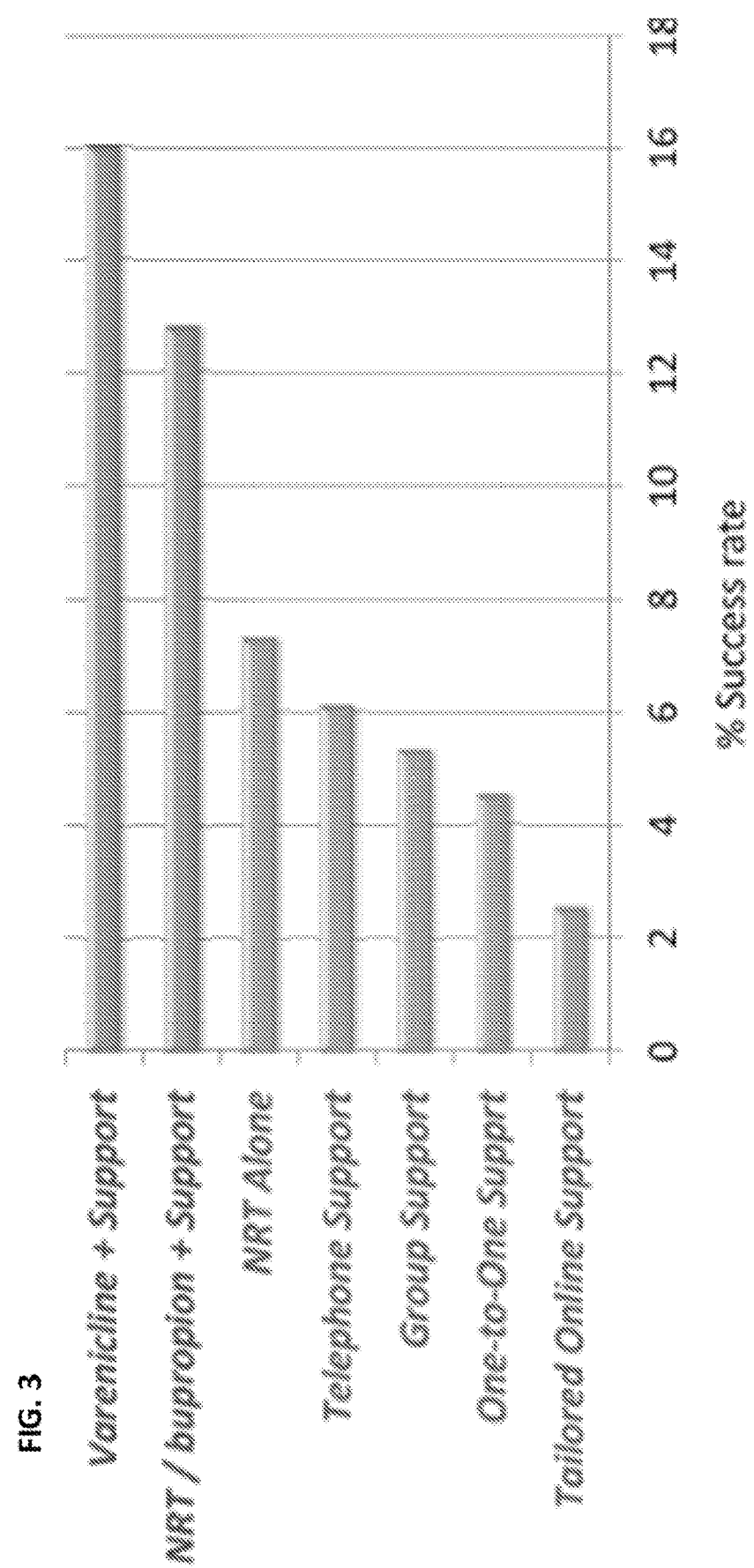
FIG. 3 is used to illustrate effect of social support on behavioral therapy.

Accordingly, FIG. 3 is used to illustrate effect of social support on behavioral therapy. In FIG. 3, how social support quadruple the success rate in a smoking cessation study in comparison with other methods is shown.

Figure 4:
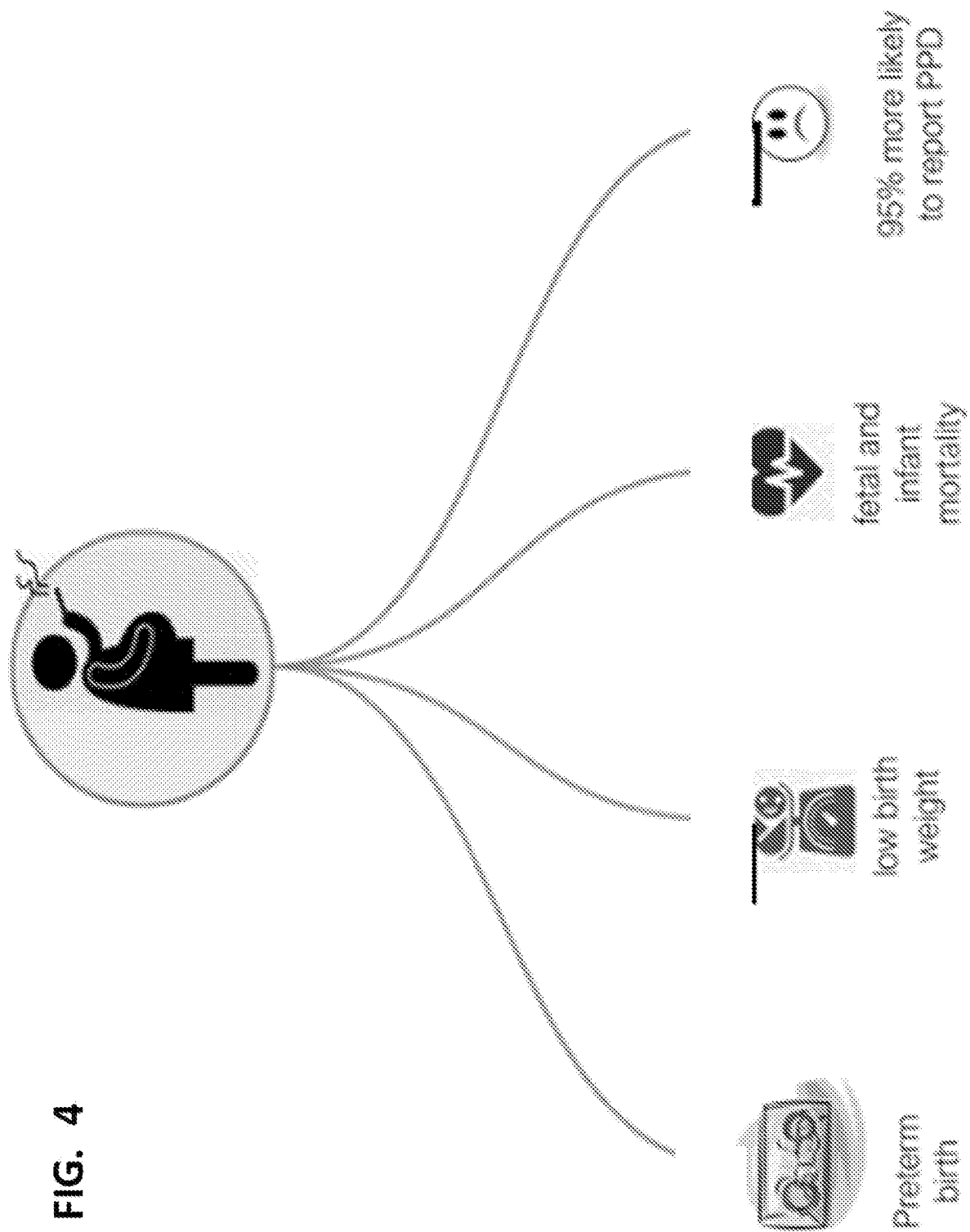
FIG. 4 is used to illustrate effect of smoking addiction on pregnant woman and her baby.

FIG. 4 is used to illustrate effect of smoking addiction on pregnant woman and her baby. In FIG. 4, for example, interdependency between smoking and post-partum depression (PPD) and other factors, and the like, calls for a sophisticated design and treatment approach, and the like. According, the illustrative Medical Platform of the present invention offers a multi-chronic condition, self-health-management application built on artificial intelligent engine to further advance patient support and research, and the like. Such a Medical Platform can be based on open-architecture to ensure future scalability and flexibility. For Patients with Chronic conditions, there is provided a virtual place to track their treatment progress and collaborate with their care team for better outcome and referred to as PerSoN (e.g., as further illustrated in FIG. 6).

Figure 5:
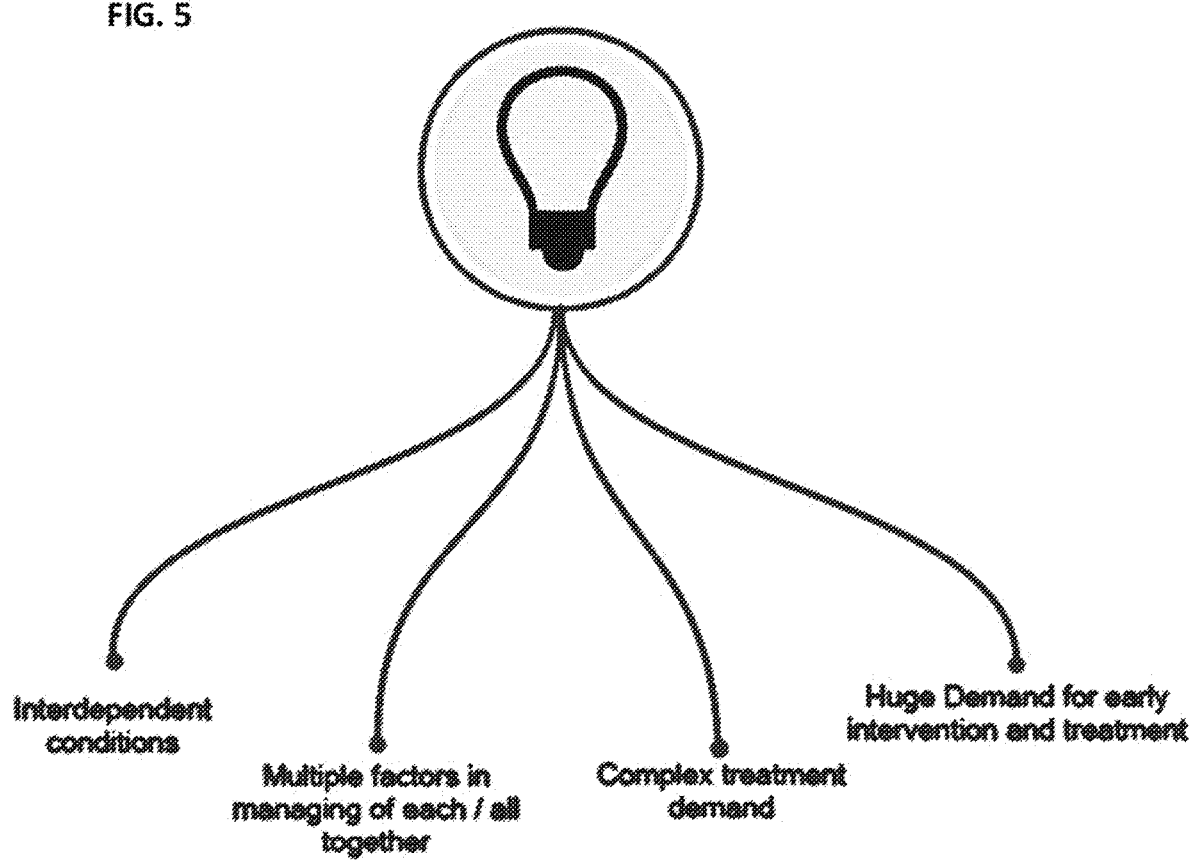
FIG. 5 is used to illustrate factors contributing to chronic conditions.

Accordingly, FIG. 5 illustrates factors contributing to chronic conditions, and the like, and FIG. 6 is used to illustrate a system and method for a patient centric, collaborative, chronic condition engagement and management platform. In FIG. 6, for example, a patient interface 602 and care provider interface 601 are provided. Care provider and researchers can remotely monitor patient reported outcome and interact with patient within secure communication platform and provide counseling service at any suitable time, location, and the like.

FIG. 7 is used to illustrate a comprehensive patient remote monitoring dashboard for a researcher and a care provider. In FIG. 7, a Care provider and Researchers interface 702 is provided, wherein the care provider and/or researchers can view, for example, in real time, patient reported outcome 702 for different health modules relevant to a patient, for example, including smoking cessation 701, depression and chronic pain and symptoms modules, and the like.

FIG. 8 is used to illustrate a Patient Controlled Health ECO-system (PCH ECO-system) infrastructure. FIG. 9 is used to illustrate a voice enable personal assistant of the PCH ECO-system. In FIGS. 8 and 9, the PerSoN Clinic components are configured, for example, as a distributed technology platform that can include any suitable hardware, devices, and the like (e.g., Bio-Sensors, PerSoN Robotics, PerSoN pins, PerSoN Towers, Body Area Networks, Brainwave sensors, PCH ECO computer hardware), software (e.g., Machine Learning engine with fuzzy logic database modeling, Artificial Intelligent engine, voice recognition engine and voice enable communication module, data collection and translation engine, PerSoN's patient mobile Interface and care provider and researchers interface), and the like.

Figure 10:
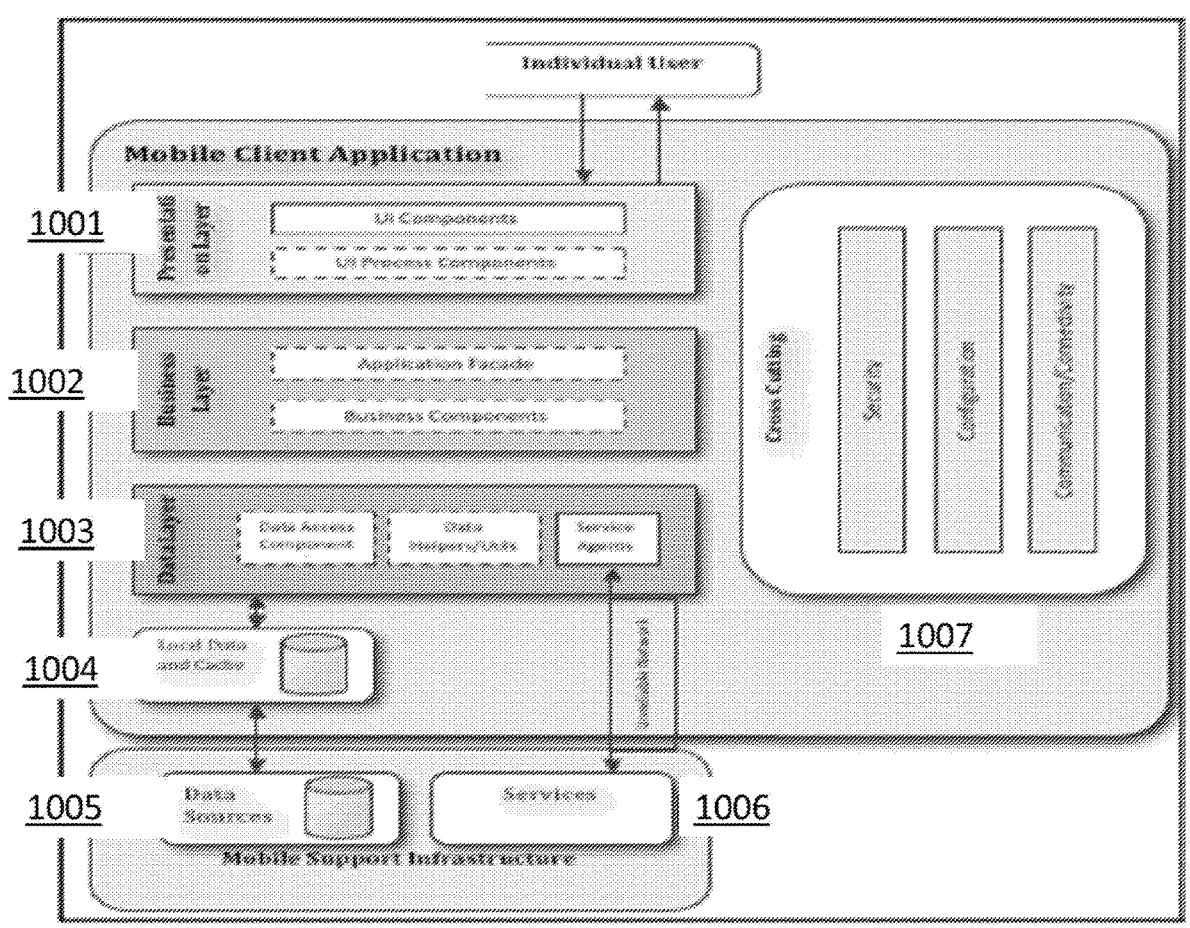
FIG. 10 is used to illustrate a technology infrastructure.

FIG. 10 is used to illustrate a technology infrastructure. In FIG. 10, a high level open architecture of PCH ECO-System can include, for example, a Mobile Client cluster having Presentation layer 1001, Business layer 1002, Data Layer 1003 and Local Database 1004. Cross cutting-edge technologies for this cluster can include, for example, Security, Configuration and Communication/Connectivity protocols 1007, which communicate with a Mobile Support infrastructure layer, including for example, Services 1006 and Data Sources 1005.

Figure 11:
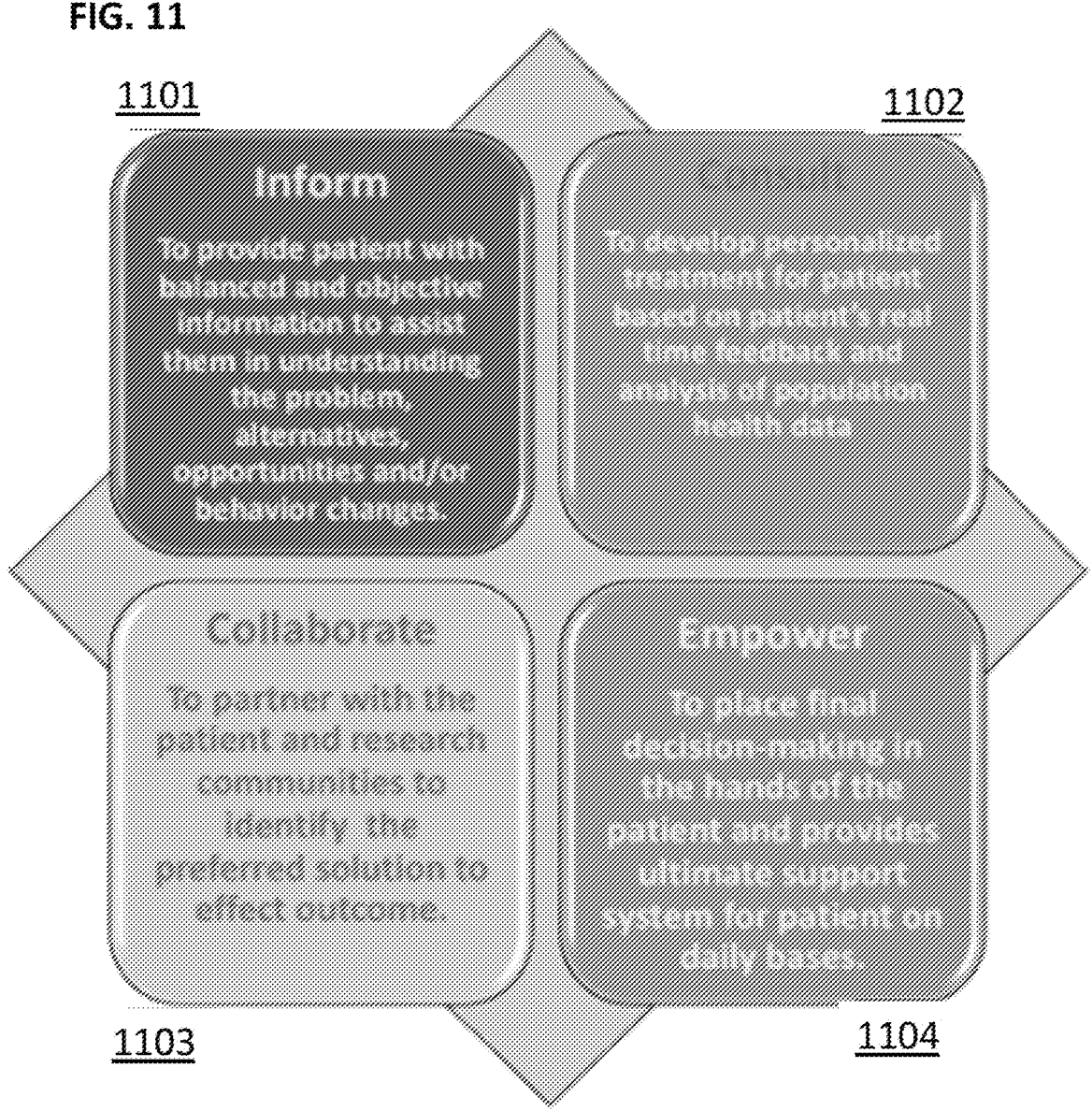
FIG. 11 is used to illustrate functioning objectives in design and development of components within the PCH ECO-system.

FIG. 11 is used to illustrate functioning objectives in design and development of components within the PCH ECO-system. In FIG. 11, guiding principles in designing various features, for example, can include:

Inform; to provide patient with balanced and objective information to assist them in understanding their problem, alternatives, opportunities and/or behavior changes 1101.

Consult; to develop personalized treatments for patients based on patient's real-time feedback 1102.

Empower; to provide an ultimate support system for patients and caregivers on a daily basis 1104.

Collaborate; to partner with the patient and research communities to identify the preferred solution to effect outcomes 1103.

Figure 12:
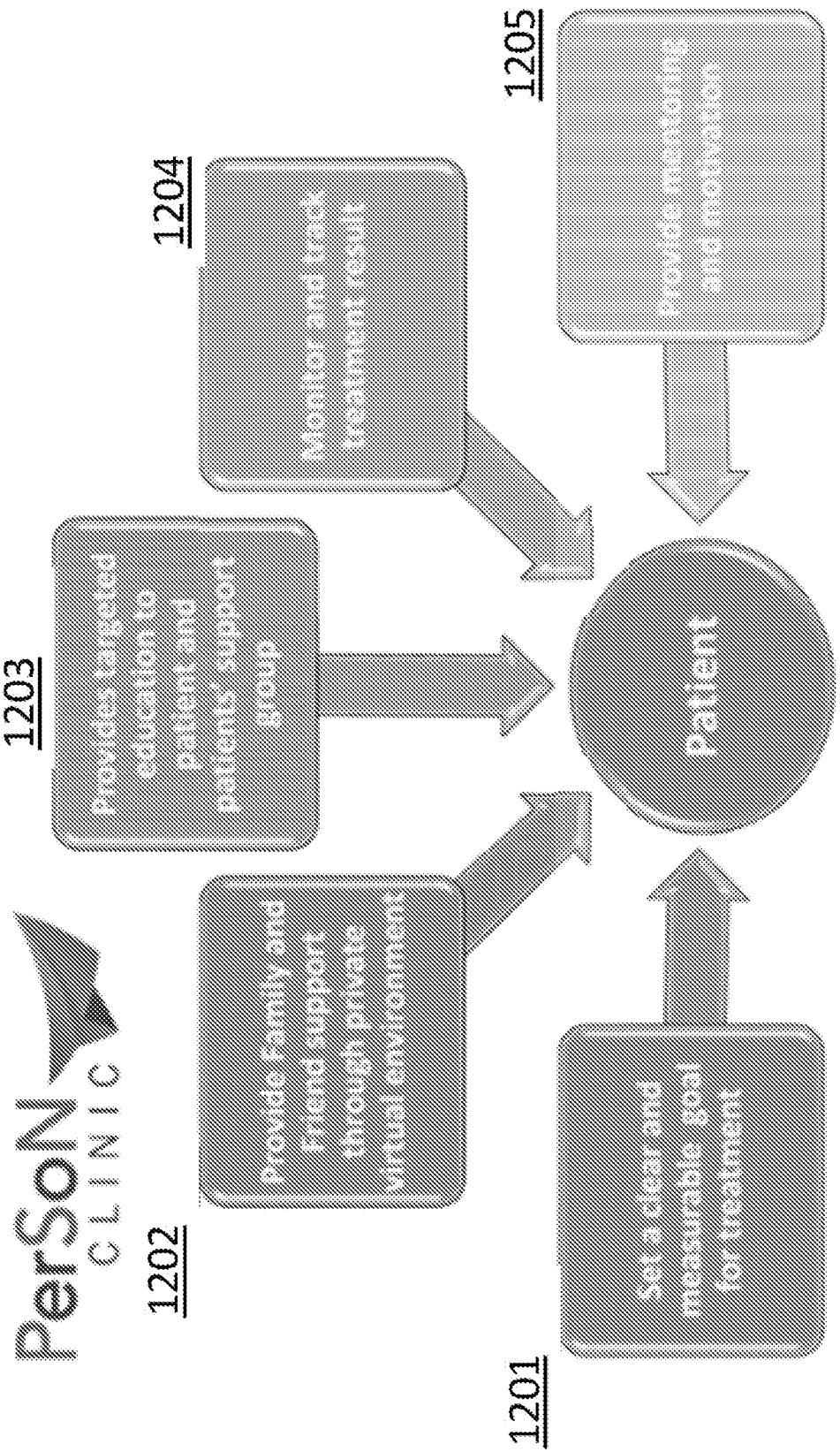
FIG. 12 is used to illustrate a set of features, advantageous, for a better health outcome.

FIG. 12 is used to illustrate a set of features, advantageous, for a better health outcome. In FIG. 12, PCH ECO-system preliminary free services to patient and their caregivers, for example, can include enabling patient to set a clear and measurable treatment goal 1201, facilitating family and friends support for patient through virtual space 1202, providing targeted and relevant education to patients and their support group 1203, enabling patients to monitor and track their treatment result 1204, and facilitating virtual mentoring and motivation 1205. Advantageously, the PCH ECO-system open architecture and modular design provides flexibility and ease of integration into any suitable care system. The PCH ECO-system novel machine learning engine 1706 can produce such outcome based on the patient's record 2001 and the output of Artificial Intelligent 2309 and personalized intervention engine 2310.

Figure 13:
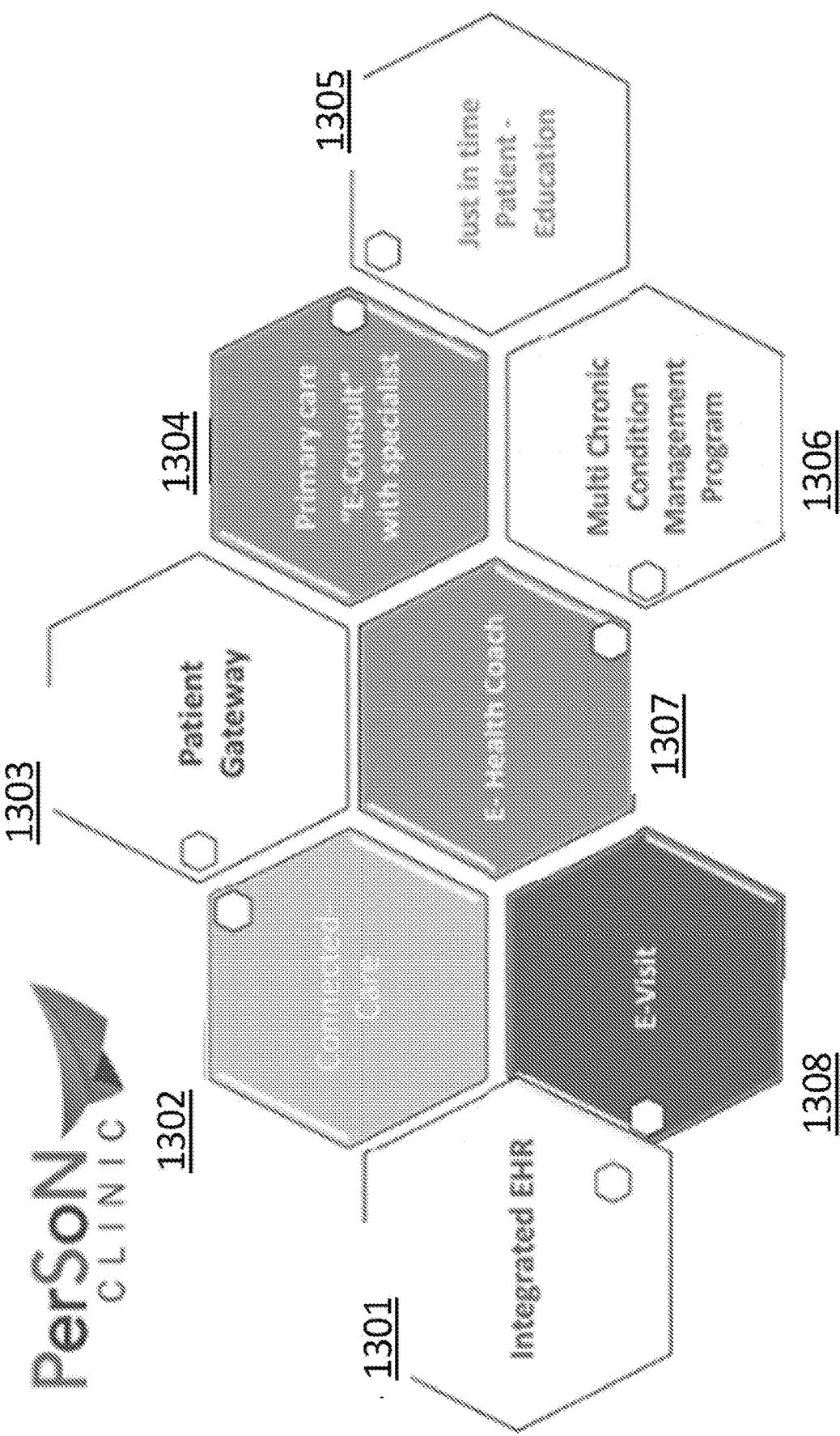
FIG. 13 is used to illustrate the PCH ECO-system integration within a hospital system.

FIG. 13 is used to illustrate the PCH ECO-system integration within a hospital system. In FIG. 13, the PCH ECO-system functional modules can operate independent of each other, wherein an Integrated EHR (Electronic Health Record) module 1301 can include HL7 and FHIR engine that enables PCH ECO-System to integrate with any suitable EHR that complies with HL7 and FHIR standards. In addition, the Integrated EHR module provides Open API to give access to the patient's record. Both Open API and Integrated HER required patient consent for accessing and/or retrieving patient records. Patient's Consent Signature can include Identifiers set by patient for every patient's provided record within the PCH ECO-System. Such identifiers define what patient's record can be shared or not with whom. A Connected Care module 1302 provides a communication hub between multiple care provider who have access to patient record in PCH ECO-system and can employ the Connected Care module for exchanging patient information. A Patient Gateway 1303 facilitate comprehensive patient interface and give patient access to their health record history. Primary Care "E-Consult" 1304 and E-Health Coach 1307, E-Visit 1308 modules can provide various levels of telehealth communications, and the like. A Patient Education 1305 module can provide patient relevant education material based using patient health records and PCH ECO-system machine learning engine (MLE)/Artificial Intelligence (AI) engine, and the like. The Multi Chronic Condition Management Program 1306 allows patient access to various health modules, for example, including: Smoking cessation, Depression management, Chronic Pain and Symptom management, Food Diet management, Medication Management, Activity Management, and the like.

Figure 14:
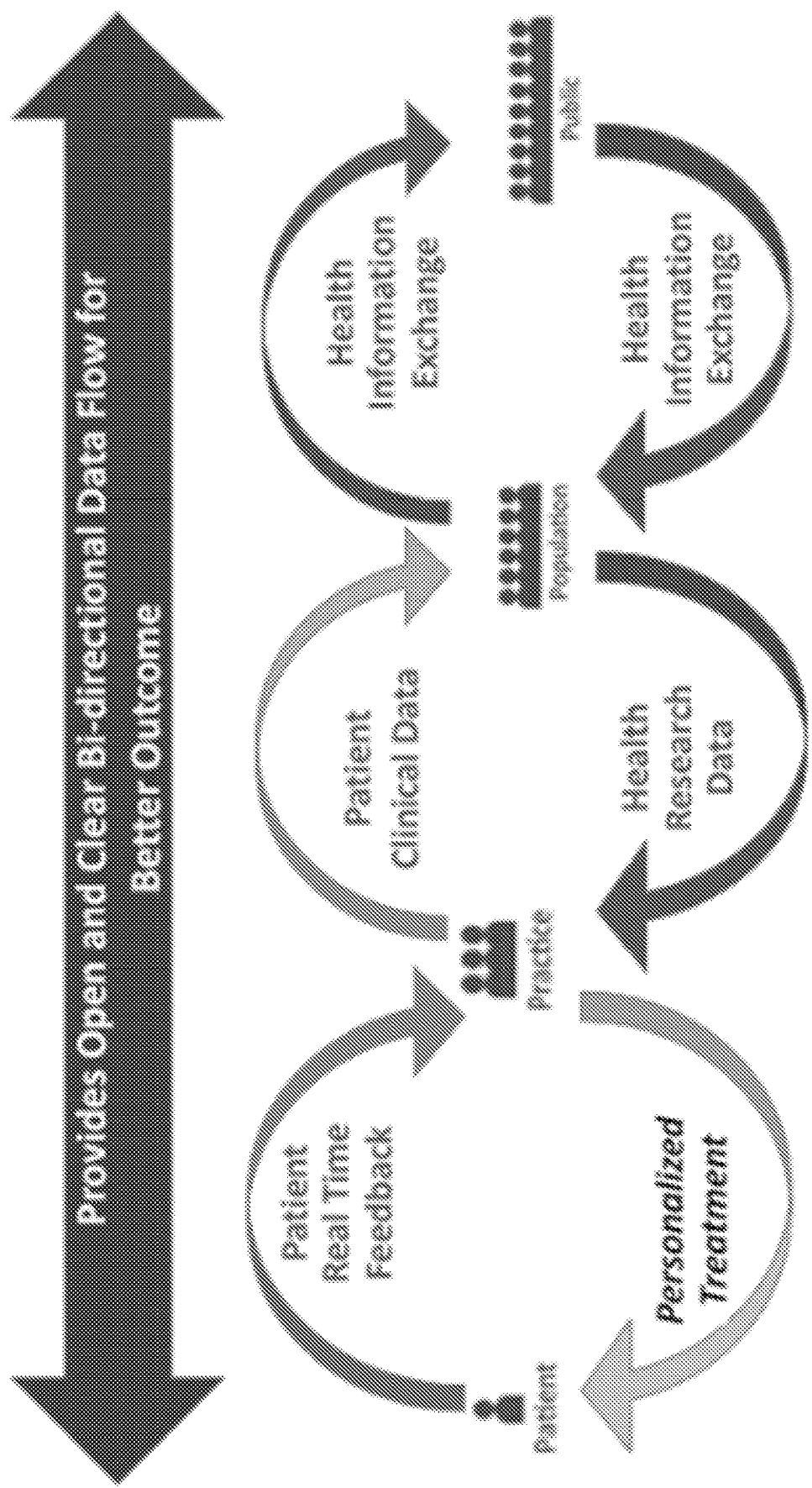
FIG. 14 is used to illustrate the PCH ECO-system data flow.

FIG. 14 is used to illustrate the PCH ECO-system data flow. In FIG. 14, the PCH ECO-system modular design with granular data collection facilitates bi-directional data flow for a better health outcome, and the like.

Figure 15:
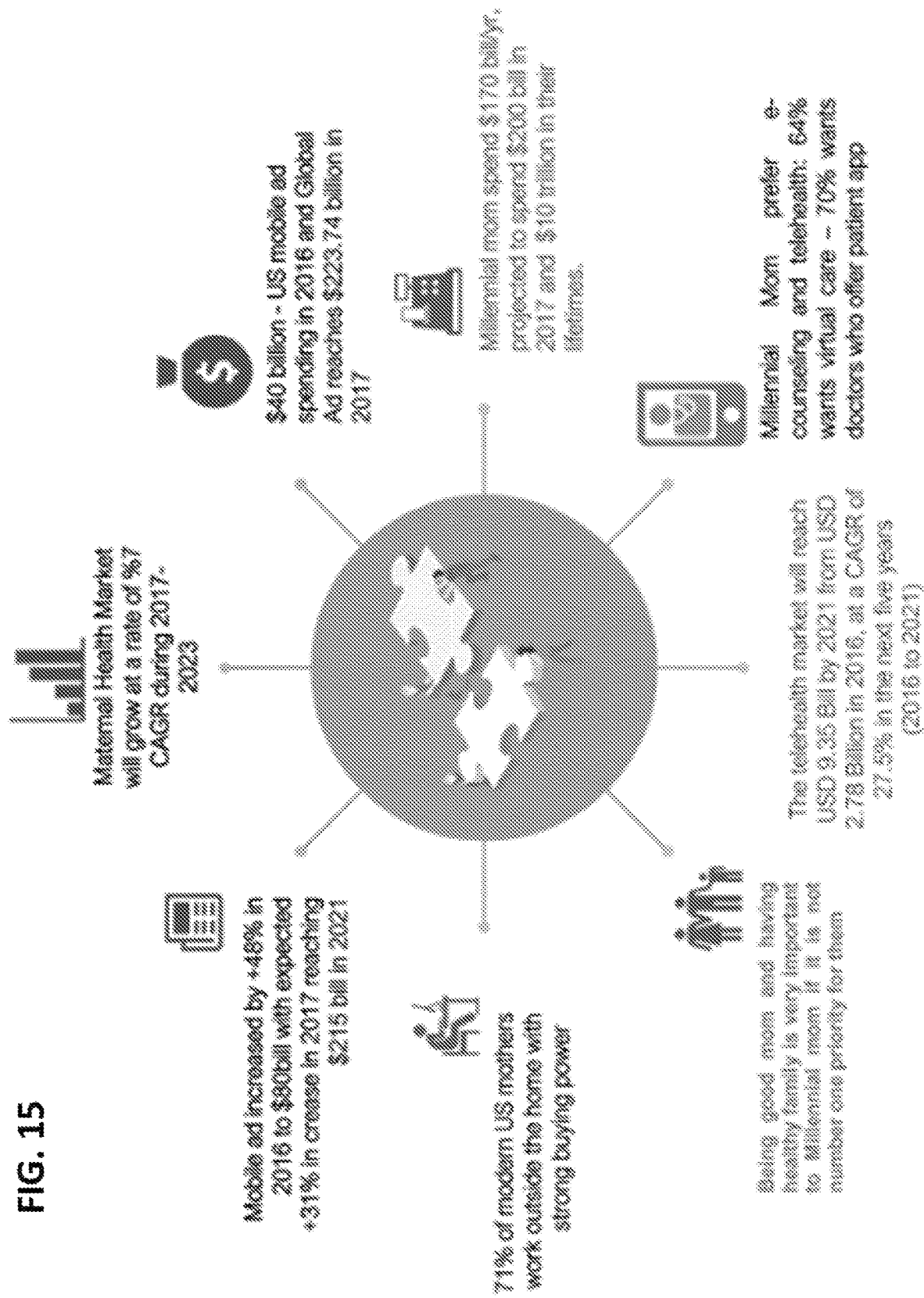
FIG. 15 is used to illustrate market analysis with a focus on a new mom.
Figure 16:
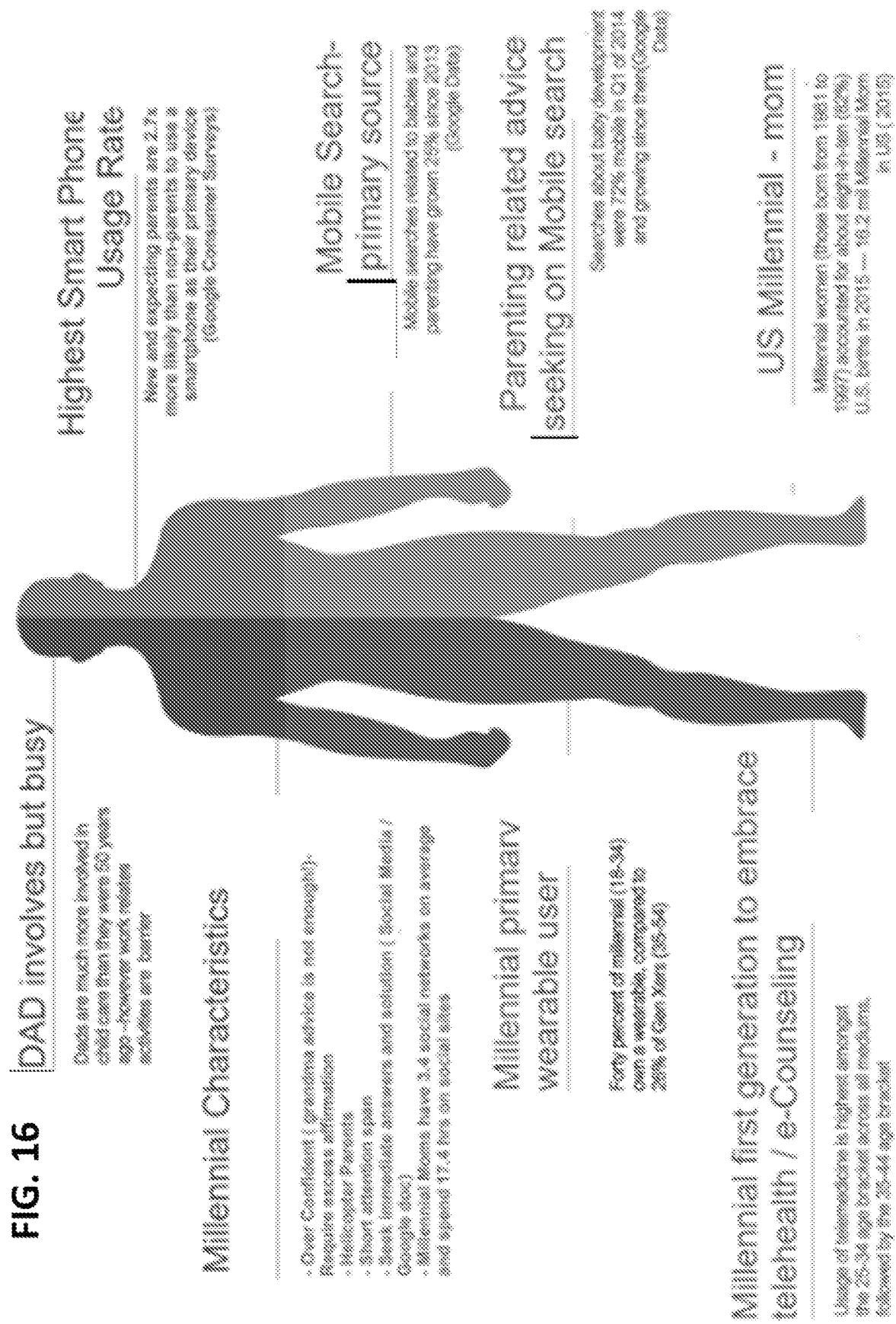
FIG. 16 is used to illustrate user expectations and behaviors with a focus on millennial parents.

FIG. 15 is used to illustrate market analysis with a focus on a new mom. FIG. 16 is used to illustrate user expectations and behaviors with a focus on millennial parents. In FIGS. 15-16, specifications of the current market with respect to millennial both as caregiver and as new parents and their unmet demand for comprehensive, affordable and connected health care system is illustrated.

Figure 17:
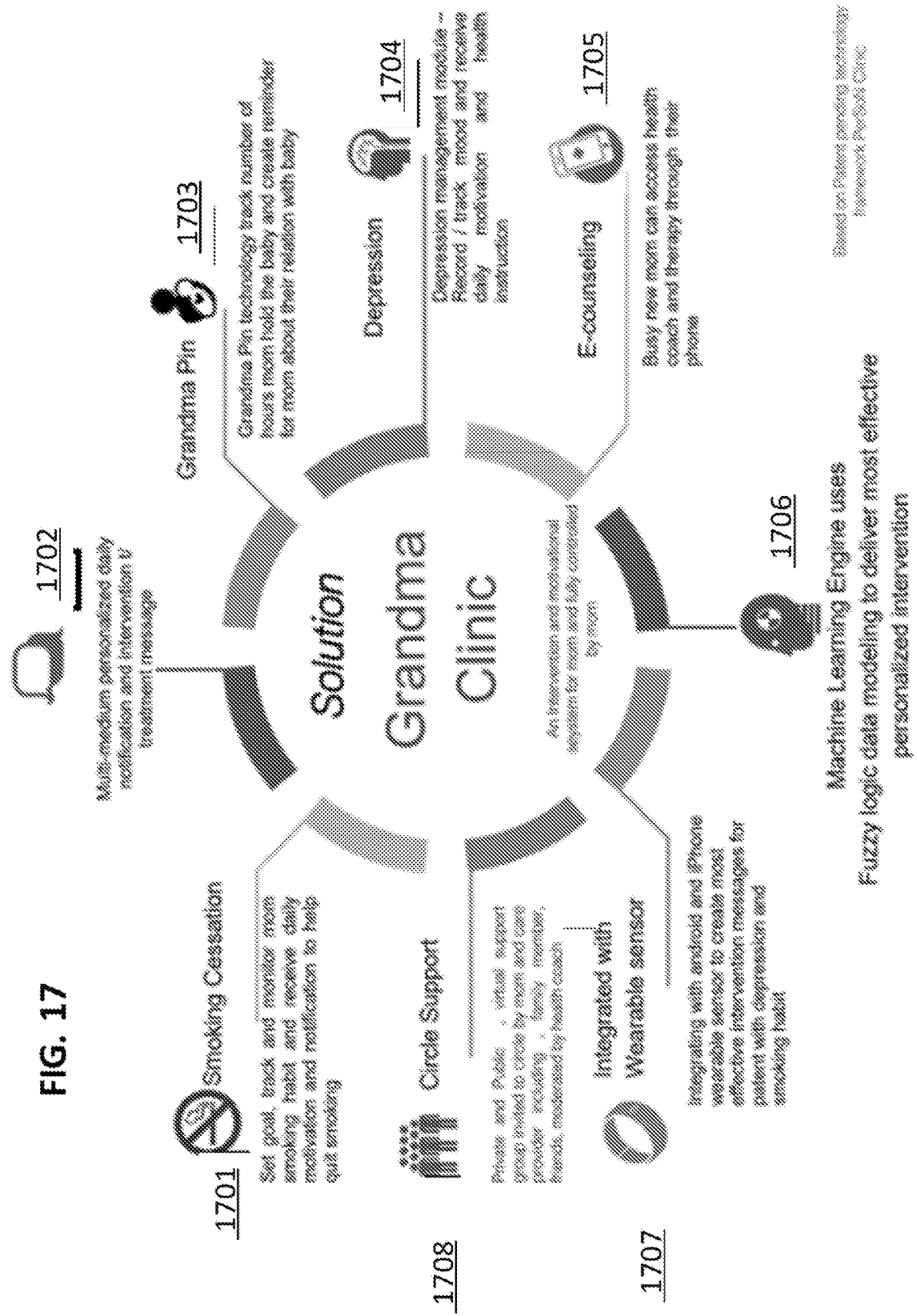
FIG. 17 is used to illustrate a customized version of the PCH ECO-system for a new mom.

FIG. 17 is used to illustrate a customized version of the PCH ECO-system for a new mom. In FIG. 17, a Grandma Clinic/Care module includes a technology platform that addresses Postpartum depression 1704, new mom isolation and smoking addiction 1701, among moms and expected moms. Real-time communication, such as WiFi technology, and the like, is provided and advantageous for real-time measurements, for analysis of the totality of the situation, and the like. For example, with Grandma pins 1703 at/on mother's dress/body, as well as the infant's, a user can monitor when and how long the baby was picked up or held by mother or baby sitter, or violent shaking by an improper baby sitter can be recorded (and e.g., with alarm provided to suitable third parties), for example, to prevent damages and monitor the health of a baby, as well as other studies to diagnose the problems with babies, through big data analysis, and the like. Such features can also be used correlate with the bonding of baby with mother, with corresponding health consequences, and the like.

The pins 1703, for example, can be configured to be aesthetically pleasing for clothing or other suitable objects (e.g., purses), to monitor events (e.g., holding a baby), to record data to analyze the data later for health or safety reasons, and the like. The smart pins can work in both directions, e.g., to measure biomarkers and to communicate to the system, or without biomarker, just measuring an event (e.g., holding a baby or a time period). For example, when a user starts feeling pain, the user can measure the intensity using biosensors 1707, such as using chemicals, such as $CO_2$ from the body for determining pain level or stress level, and the like, and used to measure and analyze the captured data more accurately. Various biosensors or bio markers can be employed, for example, for lung function or breathing. The PerSoN Pins 1707 can include communication tags (e.g., Active and Passive), and which can include bio sensors based on NFC (near-field communication) enabled or simply an NFC tags (e.g., Active and Passive). Such tags are programmed to measure and track event driven specific factors related to a health condition, which then can trigger personalized warning and/or initiate other module within the PerSoN Clinic health eco-system. Some applications of PerSoN Pin are to measure health related events, such as how long mom will hold the baby, how long an anxiety panic attack lasts, and the like. Event driven measurement of specific biomarker can be employed, such as patient respiratory rate, when pain was rated (e.g., at 9), and the like. For example, pain is very subjective measure and concept, differing in various cultures and for various people. So, to map that to the clinical definition, fuzzy logic can be employed, which can handle such types of measurements, concepts, and the like, algorithmically, mathematically, and her like. For example, behavior and pain could be modeled by fuzzy logic at 1706. The patient interacts and provides feedback to the system through suitable applications and/or personal wearable devices and bio-sensors, and the like. A patient communication/interface module, includes patient's virtual circle support 1708 that can be a built on social networking platform, and the like, and which can fully controlled by the patient, user, and the like.

This secure and private circle support social networking 1708 is one of the highly engaging modules within the system. The use of this module for patient participating in clinical trial can produce highly valuable implicit data for patient with mental health issue. For example, the patient can initiate and own such private virtual club and only patient can invite support members to his/her private club. The members of such private forum are for supporting the patient in their journeys to get better health. The system also provides training to support members on how to provide effective support. Such training modules, for example, can include static, active and interactive modules, and the like.

The system can collect all suitable communications among club members, for example, including a level of member participation, and the like, in such virtual club. Such data can produce valuable implicit data about patient and care giver's behavior. The system can conduct detailed analysis on member's words and conversation in such virtual club. The patient interface also provides access to a public forum within patient's mobile interface. Such forum is available to the public to join and participate in any suitable conversation. The system can collect detailed information on the patient and patient support member participation in such public forum.

Figure 18:
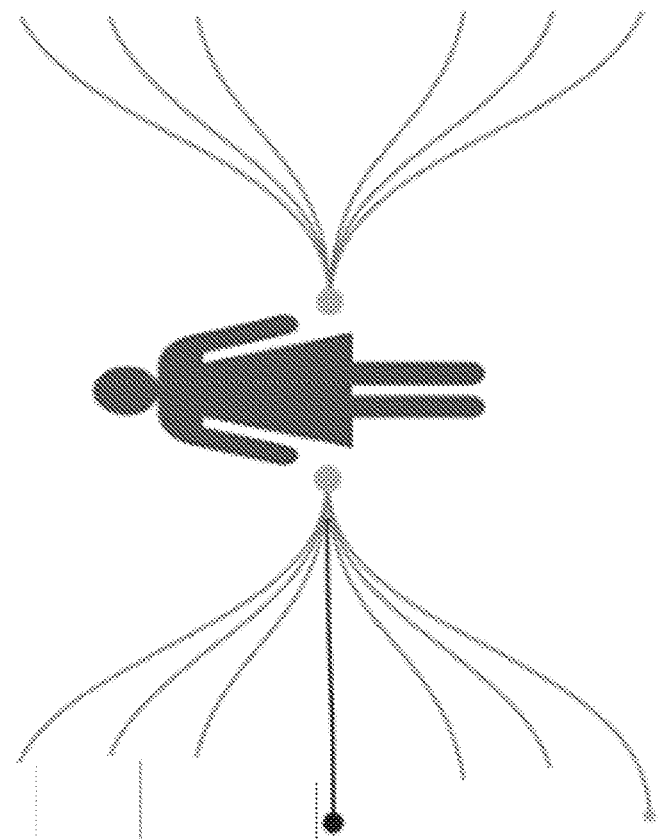
FIG. 18 is used to illustrate a two-tier service offering for a mom of the PCH ECO-system.

FIG. 18 is used to illustrate a two-tier service offering for a mom of the PCH ECO-system. In FIG. 18, various features of the PCH ECO-system within patient and caregivers interface can be made available, for example, free of charge through mobile application as Self Help at 1801. The Health Care and Health Coach 1802 provider version can be made available, for example, as a Software as a Services (SaaS) to provide a highly cost effective model.

Figure 19:
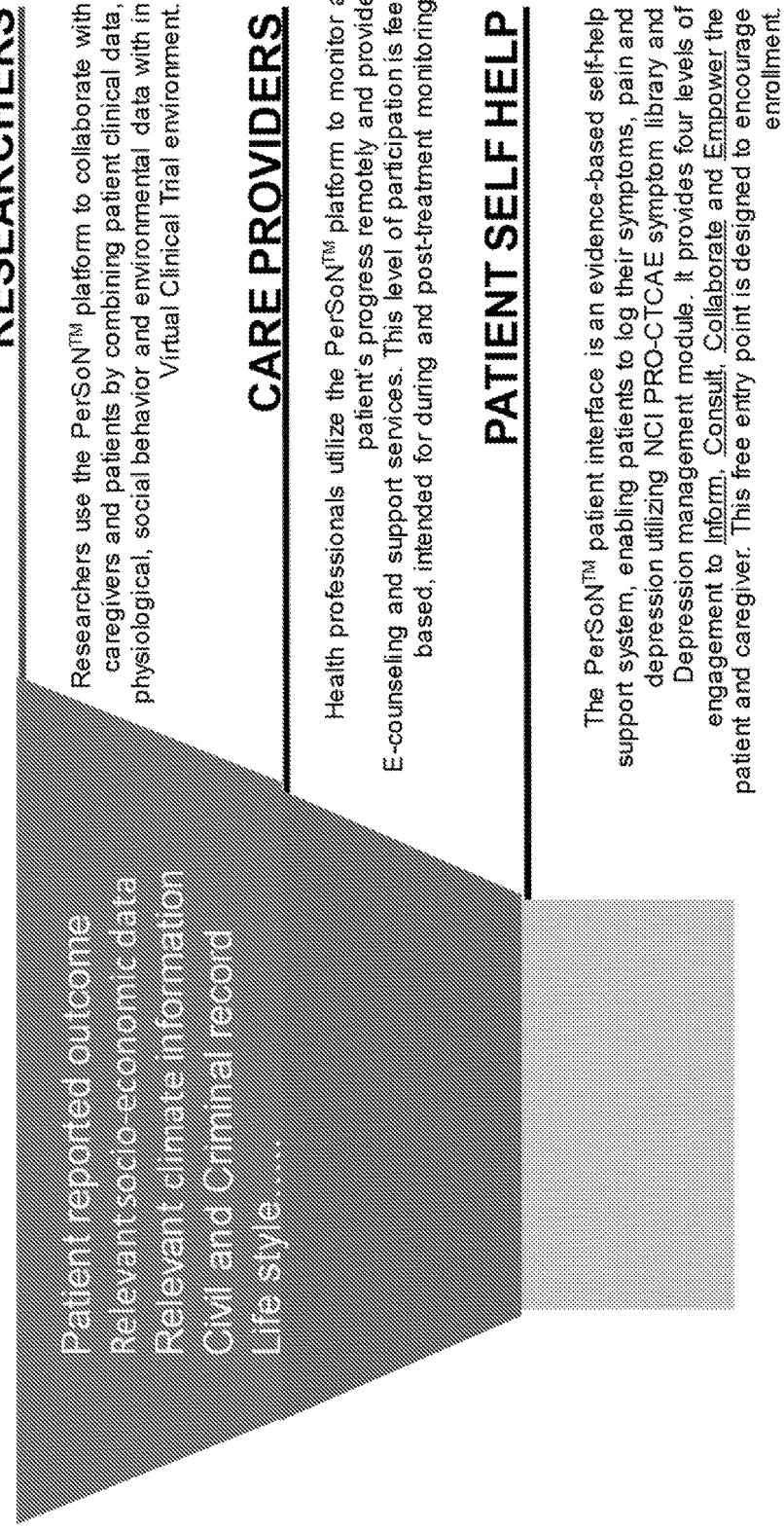
FIG. 19 is used to illustrate a general three-tier service offering of the PCH ECO-system.

FIG. 19 is used to illustrate a general three-tier service offering of the PCH ECO-system. In FIG. 19, by employing an SaaS business model, the PCH ECO-system can provide a three tear product offering. For example, Researchers can use the PerSoN platform to collaborate with caregivers and patients by combining patient clinical data, physiological, social behavior and environmental data with in Virtual Clinical Trial environment. Care Providers can utilize the PerSoN platform to monitor a patient's progress remotely and provide E-counseling and support services. Such level of participation can be fee-based, intended for during and post-treatment monitoring. Patient Self Help can be an evidence-based self-help support system, enabling patients to log their symptoms, pain and depression utilizing NCI PRO-CTCAE symptom library and Depression management module. Such a module can provide various levels of engagement to Inform, Consult, Collaborate and Empower the patient and caregiver. A free entry point can be employed to encourage enrollment, and the like.

Figure 20:
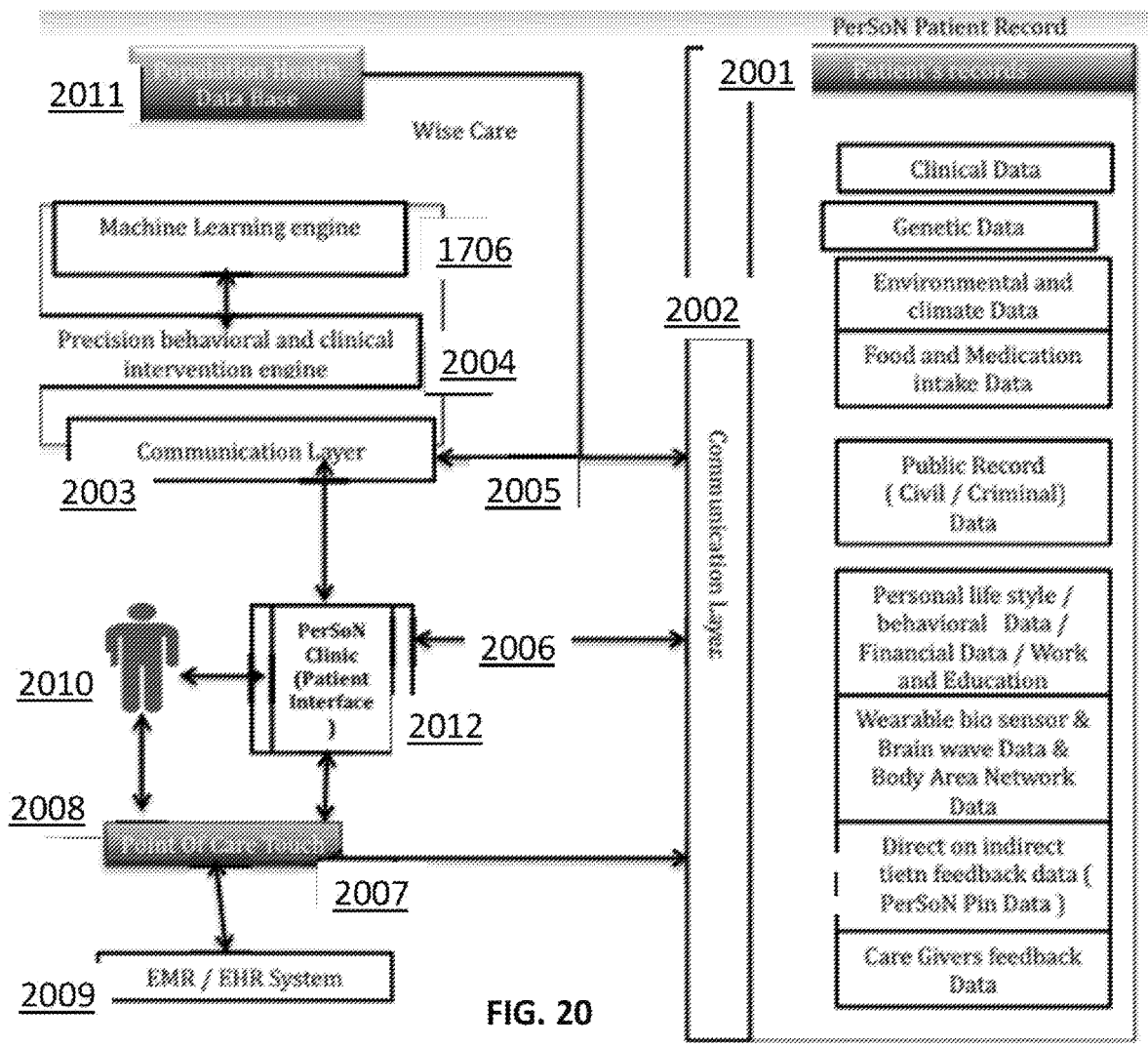
FIG. 20 is used to illustrate a high-level architecture of the PCH ECO-system.

FIG. 20 is used to illustrate a high-level architecture of the PCH ECO-system. In FIG. 20, the Patient controlled health eco-system (PCH ECO System) can be commercialized as PerSoN (Personal Support Network) Clinic, as described below:

2001—PerSon Patient's Record: The database can include individual record related to person from publicly available databases, as well as propriety databases such as labs and hospital records, including the following information: Person's Clinical data; Person's Genetic data; Environmental data from current and past person's locations; Person's civil and criminal, financial and education records; Self-reported person's life style and behavioral data, as well as collected data from person's public record (e.g., shopping and reading behavior, sports, traveling, and art interests); and Event driven personal biomarker data, including bio sensor and brainwave data, and the like.

2011—Population Health Database is aggregated collection of publicly available health data and patients' record 2001. By collecting public health data information and correlating with the person's record, the machine learning engine can predict the person's behaviors and assist the Intervention Engine to create most effective intervention methods for the Person.

2012—The PerSoN patient interface as a mobile application and related hardware devices can include PerSoN pin and PerSoN Robotics. The PerSoN application is Mobile application that runs on individual's (e.g., Patient and/or public user of PerSoN application) phone and communicate with PerSoN hardware. Such application can provide the following: Just on-time behavioral intervention; Just on-time clinical intervention; Personal bio sensor data collection; Personal health and life style input data collection; Personalized and interactive health and life style Educational module; Personalized behavioral and clinical reporting; Personalized Virtual support community utilizing latest social networking technology; Real time communication with health and life style providers; and Real time, any time, any place coaching, and the like.

1706—Machine Learning Engine: a suitable algorithm that collects personal information from and combined them with public information to create personalized predictive analysis and feeds to precision intervention 2004.

2004—The core of Precision Behavioral and Clinical Intervention Engine is an algorithm that uses aggregated patient data to optimized Active data Modeling system over time and create personalized behavioral and clinical intervention, based on up-to-date collected, and provides just on time intervention and/or treatment. This system uses latest evidenced based treatment and intervention approaches and combines it with patients' provided feedback to create personalized intervention.

2002 and 2003—Communication Layers: These modules facilitate communication and data exchange between different internal and external databases, health modules and biosensors and brainwave sensors, wearable devices and PerSoN's NFC enabled bio sensors and NFC pins.

2008—Patient uses Point of Care Touch box, which contains PerSoN Clinic hardware and software solutions and wirelessly connects local EMR and/or HER Database to patient's record by capturing Patient ID (e.g., Patient Personal Biometrics ID or unique ID) from patient through various means, including Contactless connection and/or Patient touch.

2010 Patient communicates with PerSoN modules and system by direct communication through PerSoN application (e.g., both mobile and watch), PerSoN pins, wearable and/or sensor devices.

2001—PerSoN Pins are communication tags (e.g., Active and Passive) which can be a bio sensor NFC (e.g., near-field communication) enabled or simply an NFC tags (e.g., Active and Passive). Such tags are programmed to measure and track event driven specific factors related to a health condition, which then can trigger personalized warning and/or initiate other module within the PerSoN Clinic health eco-system. Some applications of PerSoN Pin are to measure health related events, such as: How long mom will hold the baby?; How long an anxiety panic attack last?; Event driven measurement of specific biomarker, for instance patient respiratory rate, when pain was rated (e.g. at 9).

The specialty group is created, utilizing PCH ECO System technology framework, to address specific health issue, for example, including subcomponents of the platform or system:

1—PerSoN Clinic (Personalized Support Network Clinic) is used as multi-chronic condition management system. One of the versions of this system focuses on managing three conditions: smoking addiction, pain and depression. These conditions are highly comorbid and system can produce most effective and personalized intervention by engaging patient on daily basis.

2—Grandma Clinic/Care is the technology platform that addresses Postpartum depression, new mom isolation and smoking addiction, among moms and expected moms.

3—Rare Clinic: in this version, the patient with rare disease volunteers to try a specific drug and provides her feedback for better understanding of the disease and effectiveness of the drug and/or treatment methods.

4—FDA Clinic: this is a patient-centric virtual FDA that facilitates a global clinical trial for a specific drug.

Such systems can be configured as multi-lingual and available in different languages. The system and clinical/psychological solutions are designed to cure or prevent or diagnose or suggest a plan. So, they are based on patient's background, and thus, they are culturally sensitive, based on e.g. ethnicity, language, sex, education, or prior experiences. They generate advantageous message or solution for intervention or cure. So, the patient/user has pure data or physical data getting separated or distinguished from overall data, so that they can be analyzed separately with respect to other humans/prior data/experiences/history, for a better diagnosis and cure. For example, pain is very subjective measure and concept, differing in various cultures and for various people. So, to map that to the clinical definition, we need fuzzy logic, which can handle these kinds of measures/concepts mathematically. For example, behavior and pain would be modeled by fuzzy logic.

The Patient controlled health eco-system, is the multi-lingual Human centered communication and support system for collecting human's related data and feedback, directly or indirectly, actively or passively, through patient interface and/or devices, to aggregate population health database with patient data including but not limited to clinical, genetic, life style, financial, social and civil behavioral dataset through distributed communication protocol within PCH ECO-system, to be used for Active Data Modeling and to train PCH ECO proprietary Machine Learning Engine and Artificial Intelligent Engines for providing behavioral and clinical intervention notice in the form received by one or multiple human senses (sight, hearing, smell, taste and touch). The System provides private and public social networking, disease management modules, virtual community support and Virtual Charity Support. All the components of the system are voice enable with interactive communication through PerSoN Tower and other PerSoN proprietary devise and software. Wherein system provides researchers and health care providers interface to access patient's data and e-counseling platform. The system comprises a secure communication network for receiving a transfer of data from/to devices, data servers through secure communication protocol. The system includes built-in user voting system for every single feature that feeds system self-optimizing engine. The system gives patient access to "DESTROY" button, which enables patients to destroy all his/her data contribution to PCH ECO system indefinitely.

FIG. 20 has extensive description of the system, from overall view, as an example. For example, patient records 2001 include clinical data, genetic data, environment/climate data, food and medication intake data, public record/civil/criminal data, personal life style, behavioral data, financial data, work, education, or the like-data, wearable bio-sensor, EKG, brain wave, body area network-data, direct or indirect patient feedback data, caregivers' feedback data, or the like. The records are communicated to outside through communication layer 2002 and 2003, which connects to population health database 2011, through 2002, communication layer, as well as machine learning engine 1706, and precision behavioral and clinical intervention engine 2004, which interacts with machine learning engine 2004. These are also connected to PerSoN Clinic with patient interface 2012, which connects to the user 2010, which in turn are both connected to the point of care touch 2008, which is also connected to patient records 2001, through connecters 2002 and 2006. Point of care touch at 2007 is also connected to EMR/HER system 2009, which is the hardware that installed in, for example, a doctor's office for the user/patient to interact/interface with for her own data/info/input, and the like.

Figure 21:
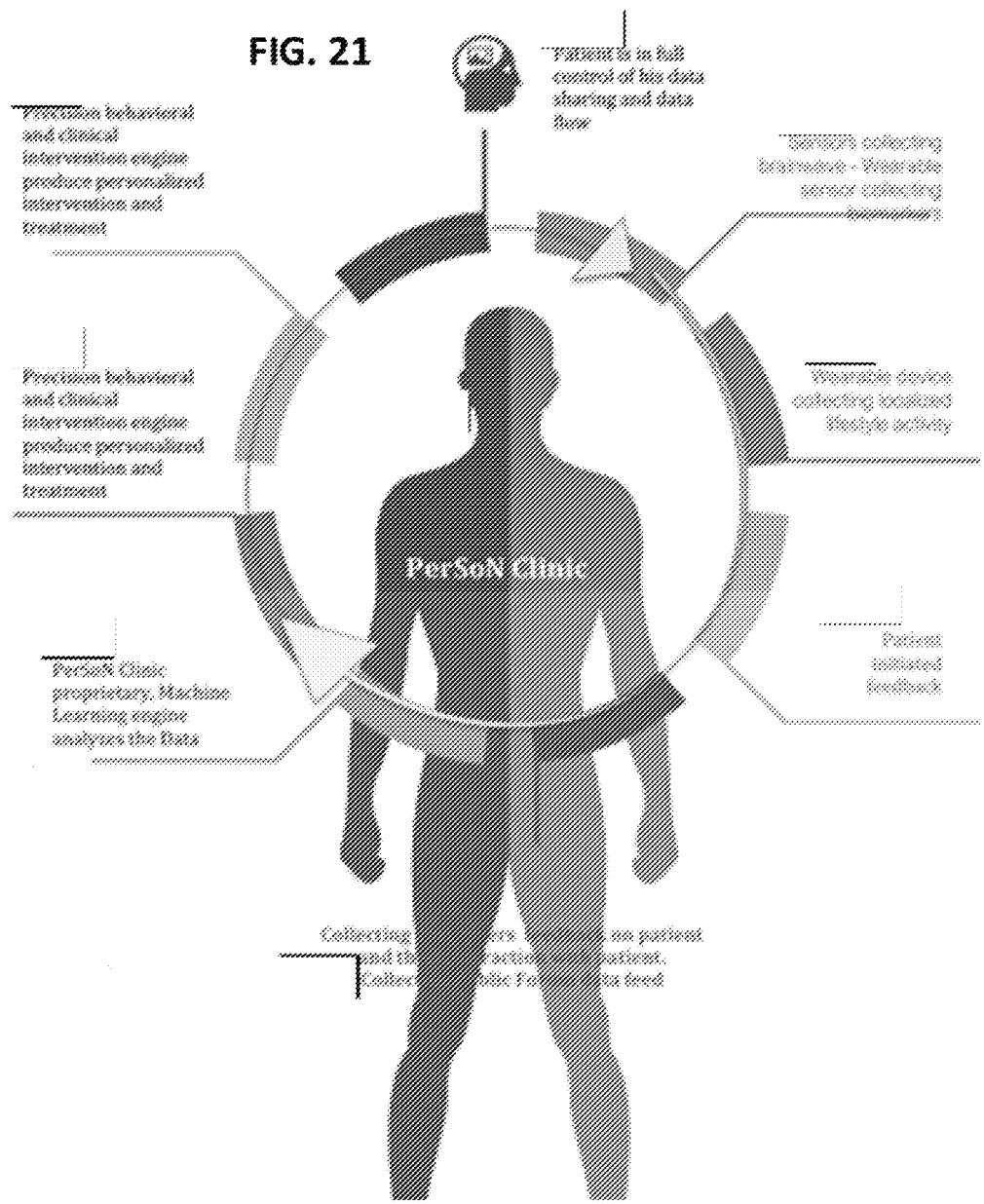
FIG. 21 is used to illustrate features and components of the PCH ECO-system.

FIG. 21 is used to illustrate features and components of the PCH ECO-system. In FIG. 21, the components of the PerSoN Clinic and interactions with other subcomponents/subsystems, in the environment/platform are shown. Such features include the patient being in control, with sensors collecting, wearable's, lifestyle activities, patient-initiated feedback, public forum data feed, machine learning engine, intervention engine, and personalized treatment, as an example. The direct feedback can be provided, for example, from the patient inputting survey or data into system, and the indirect data the comes from pin data and wearables, and the like. Feedback can be in real time, which helps the system to compare the patient with similar class or individuals for diagnosis and plan for the patient, for example, by analyzing life style and social behavior, among spectrum of factors, parameters, and people, for example, to analyze depression or probability of such event, and the like.

In one example, the doctor does not have to know the criminal records to explain or predict the environmental effects on a patient in terms of stress causing factors, and it remains private, and the machine can still do the job of the prediction and diagnosis. The Point of care touch hardware, that installed at various locations for the users, can have biometrics or unique ID/password hardware at doctor's office, for confidentiality and privacy issues. With the PerSoN Clinic hardware, the patient controls system and its input/output, in one example, so that no doctor or no insurance can break that control, for the privacy. The system provides all the suitable tools that the patient can employ to control the data and system, and the like.

The system can be employed for chronic problems, pain problems, addiction, psychological problems, clinical interventions, relationships, pain management, for pain duration, and the like. The smart pins (e.g., event driven) can be employed for recording the events and inputting the data into system, for analysis, and the like. With the smart pin a person can use the pin for communication, and can be conjured as a tag, and the like, employ Bluetooth or RFID or WiFi technologies for communication, or by any other suitable communication protocols available, wirelessly or wired/other methods, and the like. Such PerSoN's NFC enabled bio sensors and NFC pins can be used in/on various positions or items. The tags or pins can be passive or active, and they can connect to the mobile application, smart watch, smart phone, or mobile devices, such as smart key chain, and the like.

Such biosensors can measure many body functions or hormones or biological effects, for example, sweat, for stress level measurement, and the like. For example, once somebody is nervous or stressed, they can tap the sensor on their wearable device to measure the sweat, and thus, stress level, to give more objective data, versus more subjective mood or feeling from the user herself, to confirm or analyze the psychology and clinical state of a person, from various angles and through various lenses, with various metrics and thresholds, for more complete view of the situation to predict better to avoid disasters or damages, both lives and properties. Such analysis may also include be a combination of both mental and physical effects in play at a given time, in addition to context and environment around the person.

The real-time communication, such as with WiFi technology, is advantageous for real-time measurements, for analysis of the totality of the situation. For example, with pins at/on mother's dress/body, as well as the infant's, one can monitor when and how long the baby was picked up or held by mother or baby sitter, or violent shaking by an improper baby sitter can be recorded (and e.g., with an alarm sent to suitable people), to prevent damages and monitor the health of a baby, as well as other studies to diagnose the problems with babies, for example, through big data analysis, and the like. Such features can also be used to correlate with the bonding of baby with mother, with corresponding health consequences, and the like.

A server, or smart device, or smart watch, or central device or distributed farm, or any combination of the above can be employed, with various computing devices for analysis by the platform, with user interfaces and tools for the user or patient to control and get information and analysis, for the best results for prevention and cure, supported by the research of the professionals, to coordinate the analysis for medical diagnosis and cure or prevention, and the like.

The patient interface and devices can be configured to communicate with a human through one or multiple ways of human senses (e.g., sight, hearing, smell, taste and touch) and collect human data, and human feedback through one or multiple ways of human senses (e.g., sight, hearing, smell, taste and touch).

The PCH ECO-system patient interface can include voice enabled mobile interface and devices. The PCH ECO device is voice enabled system that comes in different shapes, e.g., doll, tower and/or toy pet that can be paired with pin device. The patient can pick a name for its PCH ECO device and communicate with the device by calling its name or touching it for pre-defined functions. The patient can report his/her health-related feedback through voice and touch. Such PCH ECO device can include a facial recognition module, bio-sensors, EKG sensor, CO2 and chemical detection sensors, noise, smell and motion detector sensors, and the like.

Figure 22:
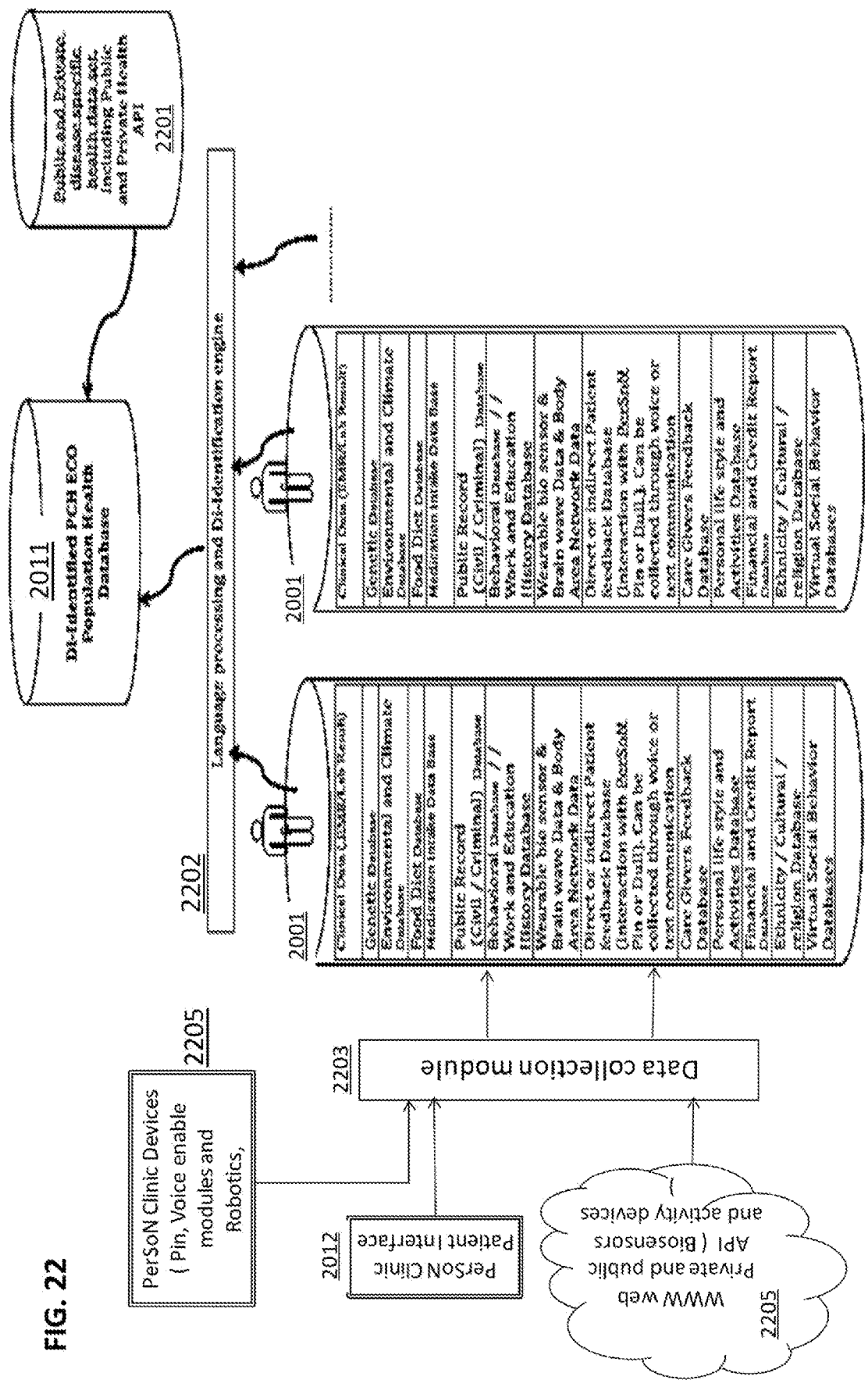
FIG. 22 is used to illustrate a high-level data flow for a populating a population health system of the PCH ECO-system.

FIG. 22 is used to illustrate a high-level data flow for a populating a population health system of the PCH ECO-system. In FIG. 22, an aggregated Population Health database 2011 within PCH ECO-system database layer is provided with patient data, for example, including clinical, genetic, life style, financial, social, civil and criminal records, and the like, 2201. A di-identification and language processing engine 2202 processes patient data as per HIPAA and GPRD regulations and translates none English patient records to English and serve as free text analyzing and processing engine. The PCH ECO-system can be connected through open and available relevant third-party health API to aggregate patient related data at 2205. The PCH ECO-system service layer also provides access to collection of PCH ECO-system API 2201 that enables researchers access to di-identified patient's health data indexed with different identifiers and or collect data from public and private relevant data APIs.

The Patient controlled health eco-system, distributed communication protocol within PCH ECO-system facilitates secure communication and data transfer with internal and external modules. PCH ECO Application Programming Interfaces (API) facilitate open communication with external system for sharing patient information with patient selected and approved, Electronic Medical Record. Research institutes can access PCH ECO di-identified data layer through designated API.

Figure 23:
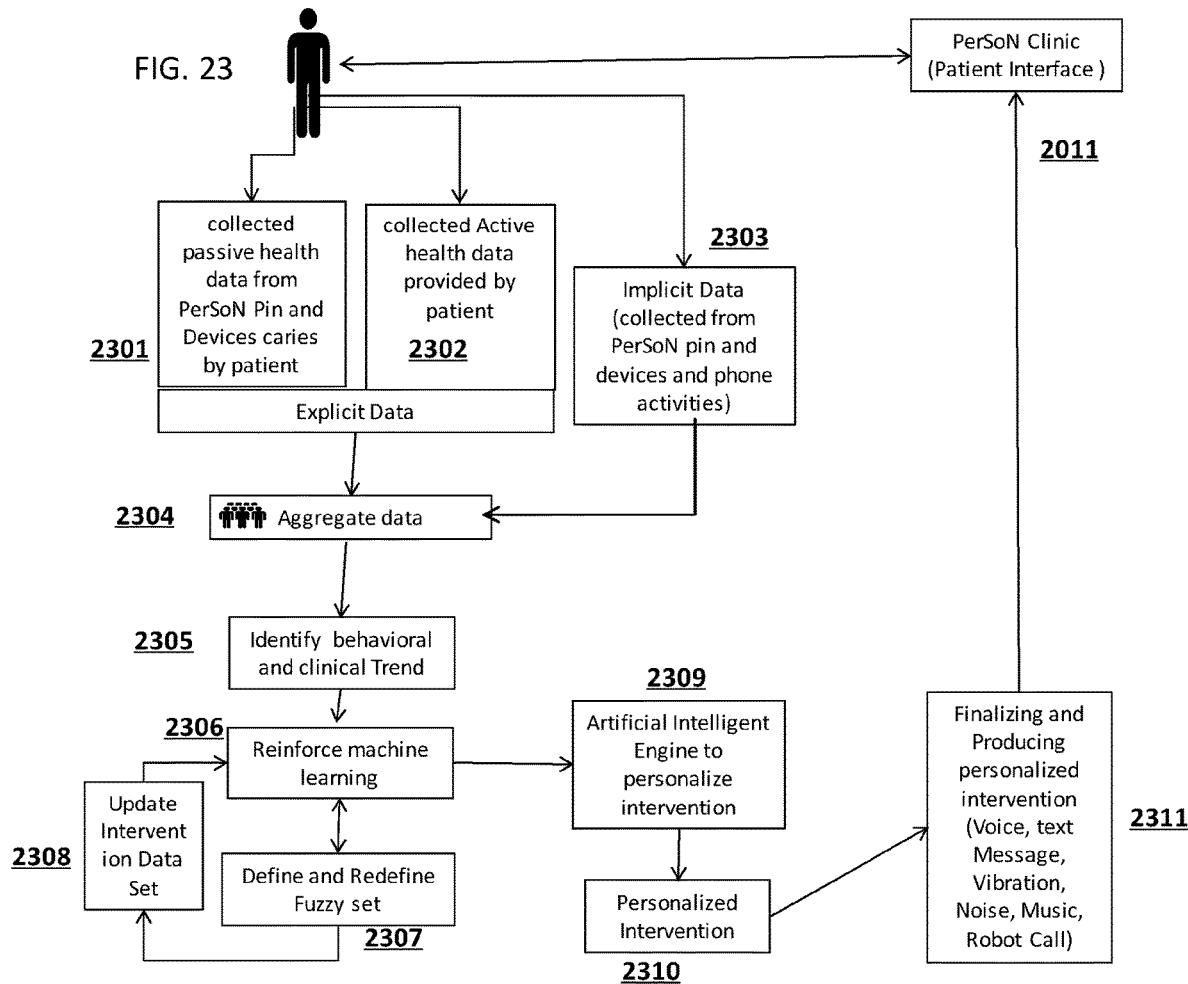
FIG. 23 is used to illustrate a high-level logical flow of sub-systems interactions within the PCH ECO-system.

FIG. 23 is used to illustrate a high-level logical flow of sub-systems interactions within the PCH ECO-system. In FIG. 23, the system collects implicit (step 2303) and explicit (steps 2302 and 2301) patient's data and aggregating such data (step 2304), for identifying the behavioral and clinical trends (step 2305) within every dataset for single or combine personal identifiers. Employed are fuzzy logic and/or neural network combinations for the collected data to analyze the system model, to obtain index value for every personal identifiers which then will be input to our Artificial Intelligent engine with proprietary method to identify relevant intervention in recommended form (step 2311).

Figure 24:
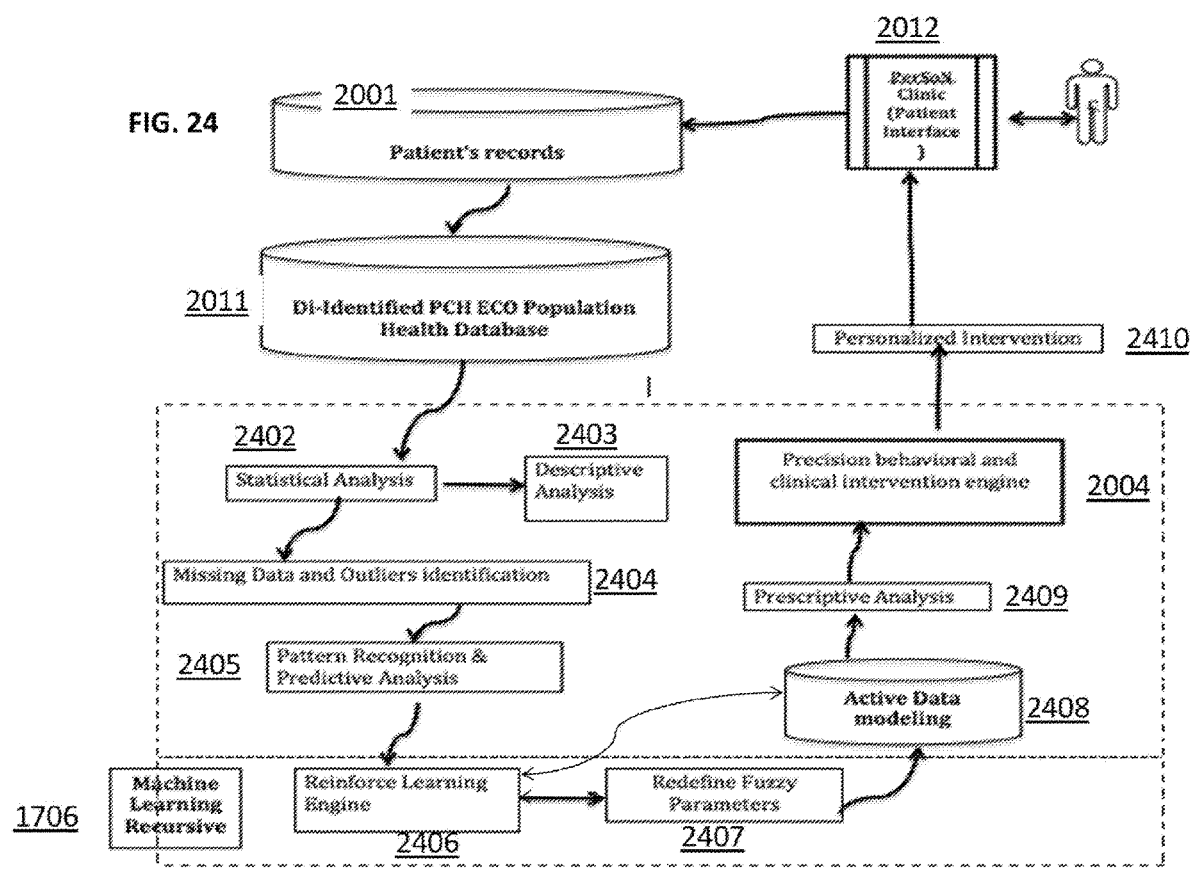
FIG. 24 is used to illustrate a high-level design system modules and engines of the PCH ECO-system and method.

FIG. 24 is used to illustrate a high-level design system modules and engines of the PCH ECO-system and method. In FIG. 24, the Patient controlled health eco-system, proprietary Machine Learning Engine 1706 and its built-in Artificial Intelligent algorithm are trained by any suitable self-optimizing methods at 2402, 2403, 2404, 2405, 2406, 2407, and 2408. The PCH ECO self-optimizing methods and modules interact with and feed to Active Data modeling system 2408, Precision behavioral and clinical intervention engine 2004, Data Analysis modules at 2402, 2403, 2404, 2405, and 2409. The PCH ECO System Active Data modeling engine 2408, for example, utilizes machine learning engine (MLE) 1706, to define and redefine fuzzy sets 2407 and create active fuzzy relational database to objectively measure personal feedback for providing personalized clinical and behavioral intervention at 2410, just in-time through mobile system and/or wearable and other devices The Patient controlled health eco-system, provides private and public social networking, disease management modules, virtual support and Virtual Charity support. While such module provides essential support for patient however, they also create wealth of implicit data regarding patient's behavior which can be used for creating more effective intervention. The disease management modules are designed based on latest scientific best practices with option for care providers to monitor patient's progress and provide intervention and feedback. The disease specific self-help health management modules, for example, including major epidemic diseases, smoking cessation and depression management with built-in user rating mechanism for every features that provide system admin with aggregated user feedback for future advancement of the system. The patient initiated private social networking (Patient Private Wall—PPW) is private virtual environment that a patient's invitee can have access to. The PPW is virtual environment that patient can have full access to. Patients can delete and destroy all the communication within that wall permanently from PCH ECO-system. The virtual community support component connects patients and caregivers with common interest and/or disease condition within their selected geographical distance. This feature enables patient within a community or neighborhood to connect and support each other. They have access to common communication features, such as one-one and group communication and multi-media media sharing. For example, the community can have access to a feature call "Remedy," every conversation can be marked as "Remedy" and voted by viewers. The "Remedy" is piece of conversation that includes health, wellness and/or lifestyle tip. Every conversation that is marked as "remedy" is searchable and can be viewed and rated by every member of PCH ECO-system and can be translated to different languages.

The PCH ECO Virtual Charity support connects patients and care givers with particular needs (e.g., financial and/or otherwise) to support groups, individuals or charity organizations capable of supporting the patient with the needs. The Patient controlled health eco-system, voice enable interactive communication is integrated into PCH ECO-system utilizes third party voice recognition technologies and optimize by proprietary PCH ECO machine learning engine at 2301.

The Patient controlled health eco-system provides researchers and health care providers interface to access patient's data in real time and e-counseling platform to connect with patients within their network as needed. Patients can define access level for multiple and each care provider. This enables a patient to be in full control of their health record data. Care providers and researchers can define the communication guidelines and venue (e.g., Online messaging, Audio or Video with in 8 am to 6 pm, only online messaging).

The Patient controlled health eco-system, includes a secure communication network for receiving and transfer of data from/to devices, data servers through secure communication protocol HTTPS, using Transport Layer Security (TLS). When PCH ECO devices communicate through WiFi the WPA2+AES security protocol will be used. The system self-optimizing engine provides usability report on every PCH ECO features by aggregating user rating data for each feature and the feature's traffic data. The system gives patient access to "DESTROY" button, which enables patients to destroy all his/her data contribution to PCH ECO system indefinitely. The PCH ECO system is fully compliance with HIPPA and GPRD privacy and security guidelines. In further illustrative embodiments, any suitable variations of the above teaching are also intended to be covered by this patent application, as will be appreciated by those of ordinary skill in the relevant art(s).

The above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, 5G communications networks, Public Switched Telephone Network (PSTNs), Packet Data Networks (PDNs), the Internet, intranets, a combination thereof, and the like.

It is to be understood that the devices and subsystems of the illustrative embodiments are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like.

While the present invention has been described in connection with a number of embodiments and implementations, the present invention is not so limited but rather covers various modifications and equivalent arrangements, which will fall within the purview of the appended claims.

What is claimed is:

1. A computer implemented system for a medical platform and for use with a user or a provider, the system comprising:
   a wearable device configured to collect implicit and explicit patient information, the wearable device including:
   an interface configured to receive implicit patient information on subjective factors such as pain or user behaviors that are provided by the user;
   at least one near-field communication sensor and biosensor, the near-field communication sensor and biosensor being configured to measure health condition factors of the user, wherein the measured health condition factors of the user are included in the explicit patient information;
   a database configured to receive the implicit and explicit patient information from the wearable device and generate aggregated patient information;
   a machine learning system configured to:
     receive the aggregated patient information from the database,
     process fuzzy logic data sets representing the subjective factors in the received implicit patient information,
     calculate index values for parameters associated with the subjective factors based on the processed fuzzy logic data sets, and
     generate personalized patient intervention information based on the calculated index values and the aggregated patient information; and
   a patient user interface display configured to display the generated patient intervention information to the user or the provider.

2. The system of claim 1, wherein the machine learning system includes fuzzy logic configured to generate a fuzzy set based on analysis of the aggregated patient information.

3. The system of claim 1, wherein the machine learning system includes an artificial intelligence (AI) engine configured to generate the patient intervention information based on the fuzzy set.

4. The system of claim 1, wherein the wearable device includes at least one of a near field communications (NFC) enabled device, a biosensor enabled device, a voice enable communications device.

5. The system of claim 1, wherein the system is configured to collect from public databases information, including at least one of civil, criminal, financial, educational, and consumer behavioral data.

6. A computer implemented method for a system for a medical platform, the method comprising one or more of the steps performed by the system of claim 1.

7. A computer program product for a method for a system for a medical platform and including one or more computer readable instructions embedded on a tangible, non-transitory computer readable medium and configured to cause one or more computer processors to perform one or more of the steps performed by the system of claim 1.

* * * * *